United States Patent [19]
Kamiyama

[11] Patent Number: 6,149,597
[45] Date of Patent: Nov. 21, 2000

[54] DIAGNOSTIC ULTRASOUND IMAGING USING CONTRAST MEDIUM

[75] Inventor: Naohisa Kamiyama, Otawara, Japan

[73] Assignee: Kabushiki Kaisha Toshiba, Kawasaki, Japan

[21] Appl. No.: 09/199,778

[22] Filed: Nov. 25, 1998

[30] Foreign Application Priority Data

Nov. 26, 1997 [JP] Japan ................................. 9-324772

[51] Int. Cl.⁷ ........................................... A61B 8/00
[52] U.S. Cl. .......................................................... 600/458
[58] Field of Search ............................. 323/234; 600/440, 600/455, 458, 456, 447

[56] References Cited

U.S. PATENT DOCUMENTS

| | | | |
|---|---|---|---|
| 5,610,509 | 3/1997 | Nustad | 323/234 |
| 5,628,322 | 5/1997 | Mine | 600/455 |
| 5,694,937 | 12/1997 | Kamiyama . | |
| 5,735,281 | 4/1998 | Rafter et al. . | |
| 5,882,306 | 3/1999 | Ramamurthy | 600/440 |

Primary Examiner—Marvin M. Lateef
Assistant Examiner—Maolin Patel
Attorney, Agent, or Firm—Oblon, Spivak, McClelland, Maier & Neustadt, P.C.

[57] ABSTRACT

An ultrasound contrast medium which substantially consist of microbubbles is injected into a patient and contrast echo imaging is performed by a diagnostic ultrasound apparatus. In the apparatus, an ultrasound pulse signal is transmitted toward the patient's diagnostic region on the basis of a changeable transmitted sound pressure, an echoed component of the transmitted ultrasound pulse signal is received to produce a corresponding reception signal, a tomographic image using the reception signal is produced, and the transmitted sound pressure is optimized so as to maximize a value of the reception signal. The transmitted sound pressure is a representative of the transmission power condition. For example, the transmitted sound pressure optimized is displayed. The transmitted sound pressure is, by way of example, optimized based on the reception signal corresponding to the echoed component emanating from an overall region of interest in a cross section scanned by the ultrasound pulse signal.

24 Claims, 15 Drawing Sheets

(A MOMENT WHEN MICROBUBBLES HAVE VANISHED)

(IN THE CASE OF A SHORTER INTERVAL)

(IN THE CASE OF A LONGER INTERVAL)

DIAGNOSTIC ULTRASOUND IMAGING USING CONTRAST MEDIUM

BACKGROUND OF THE INVENTION

1. Field of the Invention

The present invention relates to diagnostic ultrasound imaging based on a contrast echo imaging technique for acquiring a tomographic image from a reception signal including an echo reflected from a contrast medium injected into a subject to be diagnosed.

2. Discussion of the Background

Ultrasound signals have been clinically used in various fields, and one of them is an application to diagnostic ultrasound apparatus. A diagnostic ultrasound apparatus acquires an image signal through transmission and reception of an ultrasound signal toward and from a subject and is used in a variety of modes utilizing non-invasiveness of the signal. One typical type of diagnostic ultrasound apparatus produces tomographic images of a soft tissue of a living body by adopting ultrasound pulse reflection imaging. This imaging method is noninvasive and produces a tomographic image of the tissue. Compared with other medical modalities such as diagnostic X-ray imaging, X-ray CT imaging, MRI, and diagnostic nuclear medicine imaging, the imaging method has many advantages: real-time display is possible, a compact and relatively inexpensive apparatus can be constructed, patient exposure of X-rays or the like will not occur, and blood imaging is possible thanks to ultrasound Doppler imaging. The imaging method is therefore most suitable for diagnosis of the heart, abdomen, mammary gland, and urinary organs, and for diagnosis in obstetrics and gynecology. In particular, pulsation of the heart or motion of a fetus can be observed in real time through simple manipulation that in as simple as placing an ultrasound probe on a patient's surface. Moreover, since patient exposure need not be cared about, screening can be carried out many times repeatedly. Furthermore, there is an advantage that an apparatus can be moved to a bedside position for ready screening.

For screening the heart or abdominal organs, contrast echo imaging has newly been introduced and spotlighted, by which a ultrasound contrast medium is trans-venous injected into a patient for evaluating the kinetics of blood flow. Since trans-venous injection of a contrast medium is less invasive than trans-arterial injection, the method is becoming popular. The main component of the contrast medium is microbubbles that act as a source of reflection of ultrasound waves. The larger the amount and concentration of injected contrast medium is, the larger the effect of contrast imaging is. However, since the bubbles are crushed due to irradiation of ultrasonic waves, the time during which the effect of contrast imaging persists is shortened. Although a contrast medium characteristic of high persistency and high durability against sound pressure has been developed in recent years, the long-term persistence of the contrast medium in a human body predictably raises invasiveness.

In the contrast echo imaging, the contrast medium (i.e., substantially bubbles) is successively supplied into a region of interest set within a patient with blood flowing. It is assumed that once the bubbles existing in the region have been crushed by irradiating ultrasound waves, the effect of contrast imaging will be maintained at the next time of irradiation of ultrasound waves by bubbles newly flowing into the region. However, in effect, the bubbles will be crushed in turn before representing intensification of luminance on tomographic images, thus lowering and weakening the effect of contrast imaging instantaneously. This is because ultrasound waves are transmitted and received, normally, as many times as a few thousands per second, there is an organ parenchyma whose blood flow speed is rather slow, or there are relatively thin blood vessels whose kinetics of blood is needed.

A technique for detecting the presence or absence of blood flow in a diagnostic region by checking if luminance is intensified by a contrast medium has been adopted for the most fundamental diagnosis using a contrast medium. For more advanced diagnosis, a technique for acquiring information of a temporal change in spatial distribution of a contrast medium in a diagnostic region by detecting the spread of a change in luminance or the extent of intensification of luminance has been adopted. Also employed is a technique for obtaining a time required for an injected contrast medium to reach a region of interest (ROI) and a temporal change in luminance of echoes deriving from a contrast medium in a region of interest (i.e., time intensity curve (TIC)) or a maximum luminance.

The contrast echo imaging can also be performed effectively with harmonic echo imaging using a non-fundamental component of ultrasound waves. The harmonic echo imaging is based on separate detection of only a non-fundamental component derived due to nonlinear behaviors of ultrasound-excited bubbles in a contrast medium. Since organs in a living body tends to cause less nonlinear behaviors, a preferable contrast is given contrast echo images.

As concerning a phenomena that microbubbles are crushed by irradiation of ultrasound waves, a paper is reported, in which a fact that an imaging method referred to as flash echo imaging (or called Transient Response Imaging) intensifies luminance is reported. Theoretically, this imaging method adopts an intermittent transmission technique reduced to, for example, a rate of one frame per second, instead of the conventional condensed scanning by which a few tens of frames per second. Micro bubbles which have been fully accumulated without crushes during each intermittent interval are vanished at a time, generating a higher echo signal.

There are two ways of injecting a contrast medium at present. One is bolus injection by which a contrast medium is injected from an injector at one time, but at a slower speed. The other is sustaining injection by a contrast medium is injected little by little over a longer interval, like instillation. The bolus injection is relatively easy to inject it, provides a higher luminance level at a peak of the curve made by which a contrast medium component reaching a region of interest, and is fit for TIC measurement, but in the bolus injection, the contrast-persisting time is rather short, and the time is not stable. On the contrary, although the latter sustaining injection needs to control an injected amount using a dedicated sustaining injector, this injection has the advantage of sustaining a constant concentration of a contrast medium in a region of interest for relatively longer intervals. Hence, using the sustaining injection, even a contrast medium diluted to some extent can have the effect of contrast imaging almost equivalent to the former injection.

Therefore, from the above discussion, it can be understood that the key factors in utilizing a contrast medium in diagnosis with ultrasound waves are intensification of echoes from blood flow and a quantitative evaluation of the kinetics of blood flow.

When comparing the conventional contrast echo imaging with the above key factors, problems of the conventional contrast echo imaging become apparent. That is, longevity of microbubbles are still short due to irradiation of ultrasound waves, which is primarily resultant from physical characteristics of a contrast medium, and quantitative estimation techniques which can easily provide more detailed information about blood flow are not provided enough.

Particularly, the former problem is not simple. In the contrast echo imaging, it does not make sense that signal to noise ratios may be increased by raising transmission outputs, as done in conventional imaging. The former problem suggests that the contrast echo imaging have an optimum transmission output at a level slightly less than the transmission outputs conventionally used. Control of transmission outputs of ultrasound waves has not been carried out from such point of view.

SUMMARY OF THE INVENTION

The present invention has been made in consideration with the above problems, and an object of the present invention is to provide a diagnostic ultrasound apparatus capable of optimum-controlling transmitting conditions of ultrasound wave pulses, enabling more effective contrast echo imaging.

A further object of the present invention is to introduce new quantitative measurement techniques in diagnostic ultrasound apparatus performing contrast echo imaging, thus enriching measurement techniques and highly-performing the measurement to provide more detailed blood flow information.

A still further object of the present invention is to realized both the above two objects.

In order to achieve the object, as one aspect of the invention, there is provided a diagnostic ultrasound apparatus comprising: means for transmitting an ultrasound pulse signal toward a subject to be diagnosed on the basis of a changeable transmission power condition; means for receiving from the subject an echoed component of the transmitted ultrasound pulse signal to produce a corresponding reception signal; means for producing a tomographic image using the reception signal; and means for optimizing the transmission power condition so as to maximize a value of the reception signal.

Preferably, the echoed component includes a component of the ultrasound pulse signal echoed by an ultrasound contrast medium substantially consisting of microbubbles and being injected into the subject. For example, the transmitting means has an ultrasound probe firing the ultrasound pulse signal and the transmission power condition is composed of a parameter that affects a level of a sound field formed by the ultrasound pulse signal fired by the probe. By way example, the parameter is either one of a driving voltage applied to the probe and the number of transmitting transducer elements incorporated in the probe.

It preferred that the optimizing means are means that optimize the transmission power condition based on the reception signal corresponding to the echoed component emanating from an overall region of interest in a cross section scanned by the ultrasound pulse signal.

It is also preferred that the optimizing means are means that optimize the transmission power condition based on the reception signal corresponding to the echoed component emanating partly from a region of interest in a cross section scanned by the ultrasound pulse signal.

Preferably, the transmitting and optimizing means are acquiring at least one of a B-mode tomographic image, a color flow mapping (CFM) image, and a pulsed Doppler mode image.

Still preferably, the apparatus comprises means for displaying the transmission power condition optimized.

As another aspect of the present invention, there is a diagnostic ultrasound apparatus applied to a subject to be diagnosed into which an ultrasound contrast medium is injected, the apparatus comprising: means for transmitting an ultrasound pulse signal toward the subject to be diagnosed on the basis of a changeable transmission power condition; means for receiving from the subject an echoed component of the transmitted ultrasound pulse signal to produce a corresponding reception signal; means for producing a tomographic image frame by frame using the reception signal; means for optimizing the transmission power condition so as to maximize a value of the reception signal; means for temporarily raising a transmission power given by the transmission power condition after the optimization thereof; and means for measuring data indicative of a time intensity curve (TIC) concerning the reception signal after the transmission power given by the transmission power condition has been raised and ten restored by the temporary raising means.

Still another aspect of the present invention, there is a diagnostic ultrasound apparatus comprising: means for transmitting an ultrasound pulse signal toward to a same portion of a subject to be diagnosed frame rate; means for receiving from the subject an echoed component of the transmitted ultrasound pulse signal to produce a corresponding reception signal; means for producing a plurality of frames tomographic images for the same portion of the subject using the reception signal; and means for deliberately changing the transmission frame rate of the ultrasound pulse signal.

Preferably, the echoed component includes a component of the ultrasound pulse signal echoed by an ultrasound contrast medium substantially consisting of microbubbles and being injected into the subject. In this case, for example, the transmission frame rate changing means is configured to change the transmission frame rate in a given rule.

It is also preferred that the changing means has means, such as a personal computer, issuing a command to change the transmission rate and being placed externally from the apparatus. The command issuing means are connected through a communication line to the apparatus.

The remaining features of the invention will be clearly understood from the following description of preferred embodiments, described together with accompanying drawings.

BRIEF DESCRIPTION OF THE DRAWINGS

A more complete appreciation of the invention and many of the attendant advantages thereof will be readily obtained as the same becomes better understood by reference to the following detailed descriptions when considered in connection with the accompanying drawings, wherein.

DESCRIPTION OF THE PREFERRED EMBODIMENTS

First Embodiment

Figure 1:
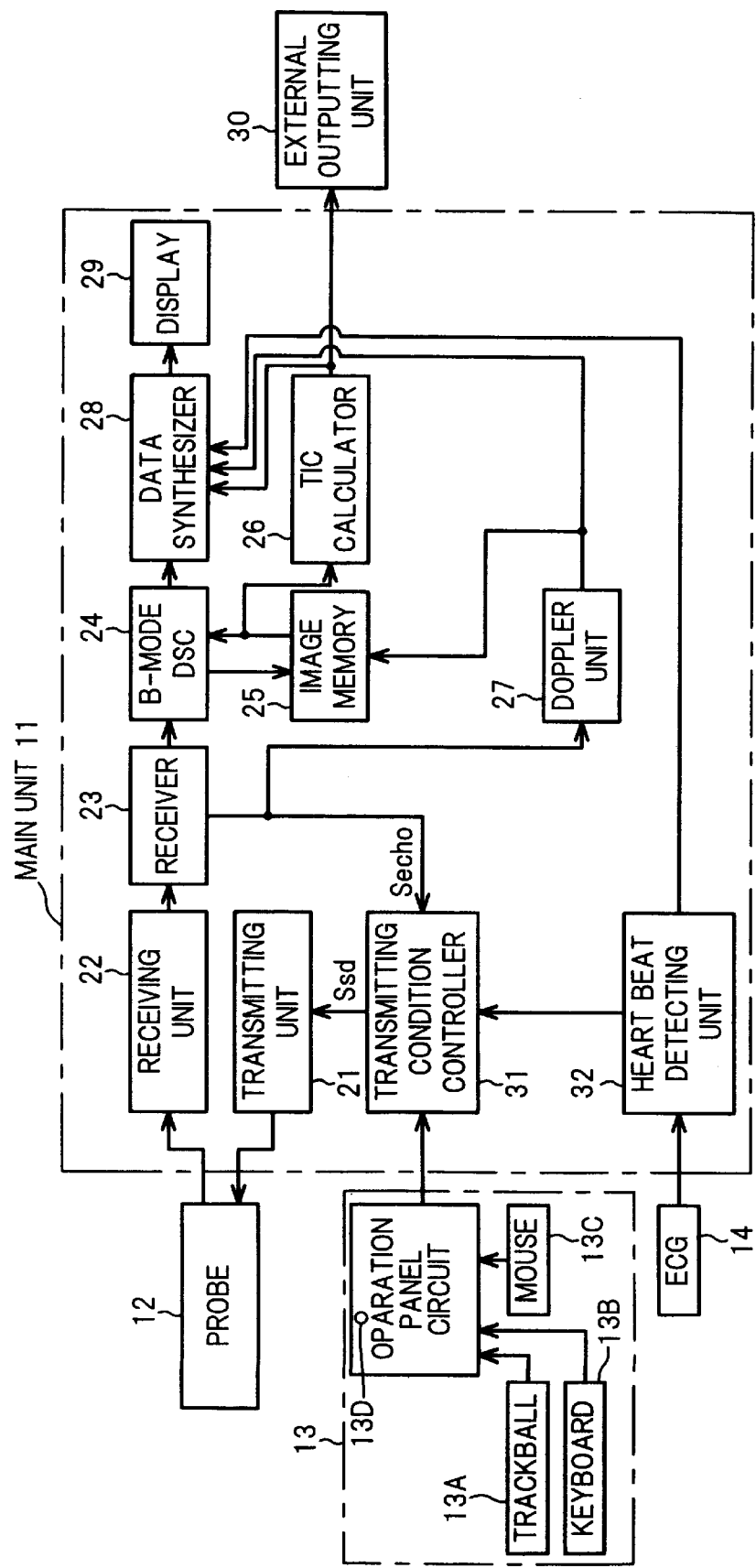
FIG. 1 is a block diagram showing a diagnostic ultrasound apparatus according to a first embodiment of the present invention.

Referring now to the drawings, wherein like reference numerals designate identical or corresponding parts throughout the several views, and wherein are illustrated exemplary embodiments of the present invention.

Figure 2:
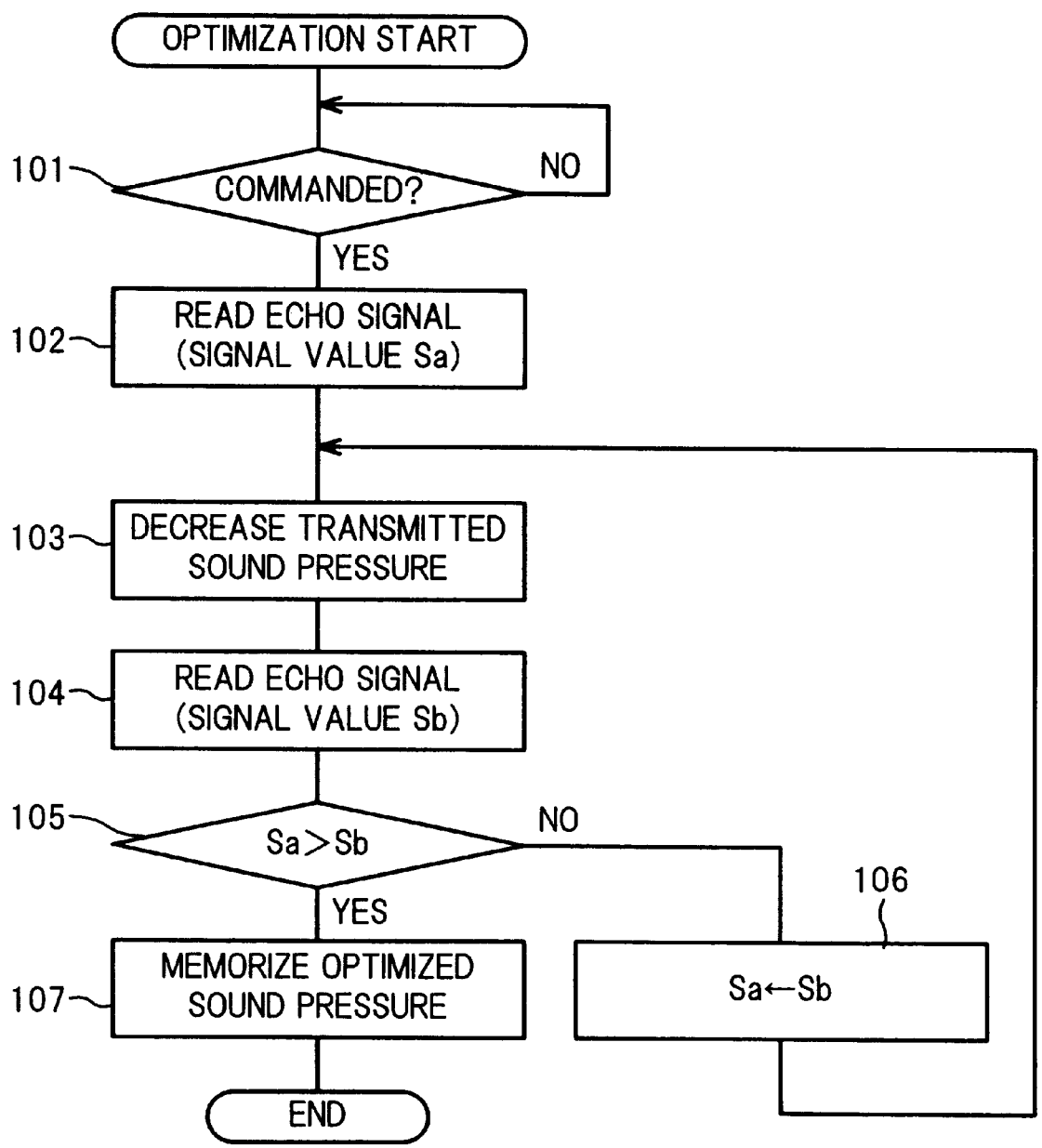
FIG. 2 is a flowchart schematically showing a control example executed in a transmitting condition controller.
Figure 3:
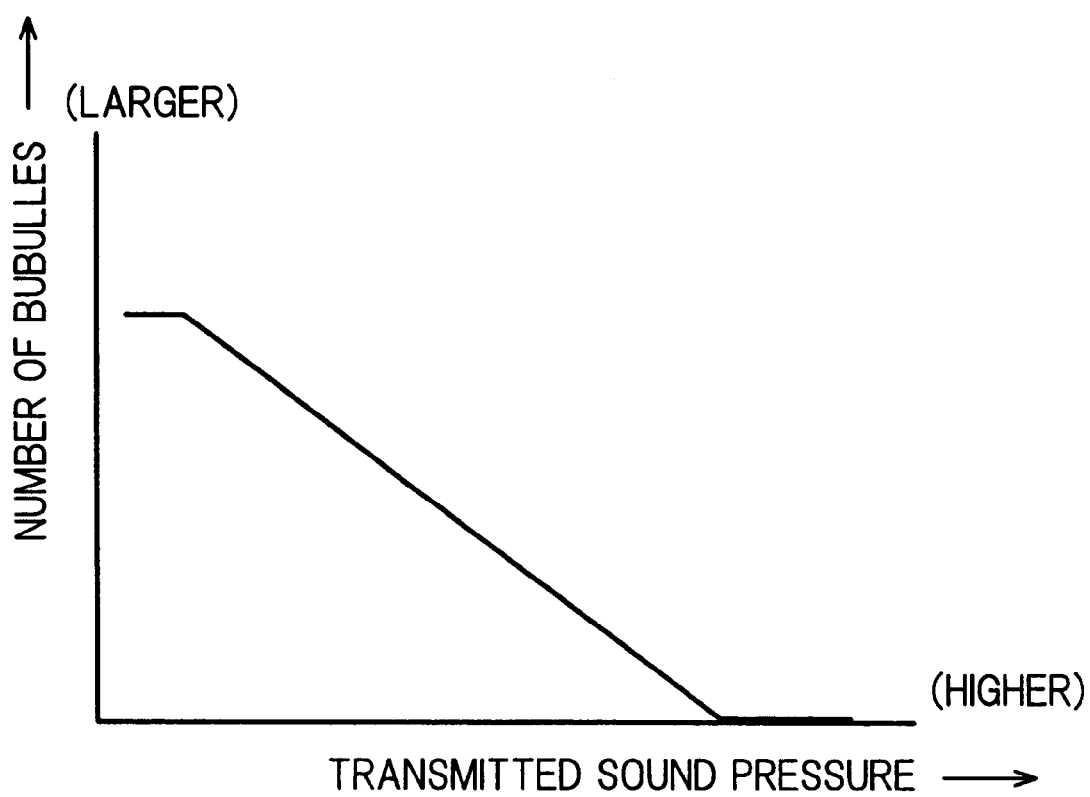
FIG. 3 represents the qualitative relation between transmitted sound pressure levels and the number of microbubbles remaining without collapse (crush) when ultrasound waves are irradiated.

Referring to FIGS. 1 to 3, a first embodiment of the present invention will now be described.

An ultrasound diagnostic apparatus according to the present invention has a configuration that provides the kinetics of blood flow from contrasted degrees deriving from an injected ultrasound contrast medium into a patient as a subject. Although the kinetics of blood flow can be observed from an entire region of interest, this embodiment adopts constituents that acquire data indicative of kinetics of blood flow based on contrasted degrees of a contrast medium inflowing into the liver parenchyma or cardiac muscle to identify abnormal regions.

FIG. 1 schematically shows the entire configuration of a diagnostic ultrasound apparatus according to a first embodiment. The diagnostic ultrasound apparatus has a main unit 11, and an ultrasound probe 12, an operation panel 13, and an ECG (electrocardiograph) 14 which are coupled with the main unit 11.

The operation panel 13 is used to give various instructions or information entered by an operator to the main unit 11. The operation unit 13 includes a keyboard 13A, trackball 13B, mouse 13C, and execution button 13D for starting optimization control of transmitted sound pressure later-described. The trackball 13B functions as a pointing device on a monitor screen as well as a device for placing a region of interest (ROI) on images. The keyboard 13A is used to command switches among "B-mode," "CFM (Color Flow Mapping)-mode," and "PWD (Pulsed Wave Doppler)-mode." The CFM mode is a mode that is able to represents two-dimensional color blood flow images.

The ultrasound probe 12, which is responsible for transmitting and receiving an ultrasound signal toward and from a patient, includes a piezoelectric transducer made of piezoelectric ceramic or the like as electromechanical bilateral converting elements. For example, a plurality of piezoelectric transducers are set in an array and incorporated in the distal part of the probe, thus constructing the phased array type probe 12. The prove 12 converts driving voltage pulses applied by the main unit 11 into ultrasound pulses and transmits them in a desired direction in a patient body. On one hand, the probe 12 converts ultrasound echoes reflected from the patient body into electric signals with corresponding voltages.

The ECG 14 is arranged to detect electrocardiograph data of a patient.

The main unit 11 comprises, as shown in FIG. 1, a transmitting unit 21 and a receiving unit 22 which are connected to the probe 12, and additionally, a receiver 23. B-mode DSC (Digital Scan Converter) 24, image memory, TIC (Time Intensity Curve) calculator 26, Doppler unit 27, data synthesizer 28, and display 29 which are placed in that order at the output stage of the receiving unit 22. The TIC calculator 26 is also connected with an external outputting unit 30 externally placed from the apparatus. The external outputting unit 30 is, for example, a printer, magnetic recording medium, or personal computer connected via a network. The main unit 11 further comprises a transmitting condition controller 31 for primarily controlling transmitted states of an ultrasound beam pulse signal from the transmitting unit 21, and a heart beat detecting unit 32 receiving an ECO signal detected by the ECG 14.

Each component in the main unit 11 will be described in detail in terms of its configuration and operation.

The transmitting unit 21 includes a pulse generator, transmitting delay circuits, and pulsars, which are not shown. The pulse generator generates rated pulses of a frequency fr [Hz] of, for example. 5 kHz (cycle is 1/fr [sec.]). The rated pulses are distributed into transmission channels and sent to the transmitting delay circuits. Timing signals used to determine delay times are sent to the transmission delay circuits channel by channel. This causes the transmission delay circuits to give command delay times to the rated pulses channel by channel. The rated pulses delayed by specified times, are then sent to the pulsers channel by channel. The pulsers generate driving voltage pulses and send them each transducer of the probe 12 at timing determined by the rated pulses, every channel, causing the probe 12 to irradiate ultrasound pulse waves. The waves are converged in the form of a beam (beam-formed) inside a patient body and have a transmission directivity thereof set to a commanded scanning direction.

In this embodiment, intervals of scanning commanded from the transmitting unit 21 is controlled by the transmitting condition controller 31, as described later. The controller 31 is one constituent featuring one of the aspects of the present invention.

A transmitted, beam-formed ultrasound pulse signal inside the patient body is reflected by a plane therein for which acoustic impedance is discontinuous. A reflected ultrasound signal is received again by the probe 12 and converted into electric echo signals with corresponding intensities. The echo signals are fetched into the receiving unit 22 for each reception channel.

The receiving unit 22 comprises preamplifiers, receiving delay circuits, and an adder in this order from the input state thereof. Delay times for the receiving delay circuits are given as a delay time pattern in compliance with a desired reception directivity. The echo signals are, every reception channel, amplified by the preamplifiers, then delay-controlled by the receiving delay circuits, before added to each other by the adder. The addition permits echoed components in a commanded direction are enhanced, thus beam-forming the echo signals by calculation. The transmission and reception directivities are taken into account comprehensively.

The output of the adder in the receiving unit 22 is connected with the data synthesizer 28 trough a route from the receiver 23 to the B-mode DSC 24.

The receiver 23 includes a logarithmic amplifier, envelope detector, and A/D converter which are not illustrated. Additionally in cases where the harmonic echo imaging is conducted, the receiver 27 further includes a band pass filter that passes, for example, only a harmonic component of double the transmission frequency of transmitted pulse waves. The receiver 23 produces the beam-formed echo signal into echo data in the digital form, and sends them to the B-mode DSC 24.

The B-mode DSC 24 converts the echo data conformable to an ultrasound scanning system into echo data conformable to a standard television scanning system, and sends the resultant echo data to the data synthesizer 28.

The image memory 25 is coupled with the B-mode DSC 24, and includes a memory device and a writing/reading controller for storing therein data handled by the DSC24 (i.e., either one type of data conformable to ultrasound scanning or standard television scanning). Echo data stored in the memory device can be read by the unit of frame during real-time imaging or after such imaging in response to an operator's command. The read data are sent via the DSC 24 and the data synthesizer 28 to the display 29 to be displayed thereon.

The read-out terminal of the image memory 25 is also coupled with the TIC calculator 26 so that the read data from the memory can be provided thereto. The TIC calculator 26 has a working memory and a calculating circuit such as a CPU, where TIC data are calculated from echo data written in the working memory, and the calculated TIC data are outputted to the data synthesizer 28, and if necessary, to the external outputting unit 30. Thus the TIC data are displayed by the display 29 and/or outputted to the external outputting unit 30.

The Doppler unit 27 receives the echo signal added in the receiver 23. The unit 27 is provided with a detector, clutter removing filter, Doppler shift frequency analyzer, calculator for average velocities and others, DSC, and coloring processor, thus providing color image data of blood flow, such as Doppler shift frequencies(i.e., velocities of blood flow) and their power values. The color image data of blood flow (CFM data) undergo processing such as noise canceling and converted in the scanning systems by the DSC placed in the Doppler unit 27. The color image data thus-processed are sent to the data synthesizer 28 and/or to the image memory 25.

The heart beat detecting unit 32 receives the ECG signal from the ECG 14 and sends its ECG signal data to the data synthesizer 28, and concurrently, produces a trigger signal for performing electrocardiograph synchronization which makes acquisition timing of heart images be synchronism with an ECG waveform. The trigger signal is sent to the transmitting condition controller 31.

The data synthesizer 28 synthesizes into frame image data a B-mode image (gray scale image) sent from the B-mode DSC 24, CFM-mode image (color flow image) sent fort the Doppler unit 27, ECG waveform data sent from the heart beat detecting unit 32, calculated data in the TIC calculator 26, and/or desired parameters used in either mode of being in parallel or superposed. The synthesized frame image data are read consecutively by the display 29, where image data are converted into the analog form by an internal D/A converter, and displayed on a screen as tomographic images of tissues of a patient.

Furthermore, the transmitting condition controller 31 includes an A/D converter and a CPU which receive operative data from the operation panel 13, as well as a memory coupled with the CPU. Data of a program for controlling transmitting conditions are stored beforehand. The CPU is coupled, through an interface, with the operation panel 13, receiver 23, heart beat detecting unit 32, transmitting unit 21, and TIC calculator 26, and executes processing shown in FIG. 2 on the basis of inputted signals, thus providing control signals.

Optimization control for transmitted sound pressure will now be described.

One preferable use of the apparatus lies in a mode in which contrast echo imaging is performed with a patient into which an ultrasound contrast medium is injected. FIG. 2 exemplifies optimization control of transmitting conditions executed by the transmitting condition controller 31 under the performance of the contrast echo imaging. The controller 31 is constructed so that it not only receives the ECG synchronization signal $S_{seg}$ from the heart beat detecting unit 32 but also controls an ultrasound beam signal to be transmitted at intervals (i.e., in a restless state) or intermittently, as described later.

As one transmitting condition, a parameter of transmitted sound pressure is selected and will be described hereinafter. In this embodiment, relevant components in the apparatus is configured to control the transmitted sound pressure by directly adjusting a transmitting drive voltage supplied to the probe 11. As concerning the transmitting conditions, it is not necessarily confined to the transmitted sound pressure, but any parameter that is capable of directly or indirectly affecting pressure in an acoustic field in a patient region to be diagnosed. For example, such an alternative parameter is the number of transmitting transducers incorporated in the probe 11.

It is assumed that transmitted sound pressure is initially set to a value used in the conventional diagnosis. Such an initial sound pressure value is, for example, 1 M Pascal which is known as an enough level to crush (collapse) microbubbles of a contrast medium. When an injected contrast medium reaches a diagnostic region, intensities of echo signals will be increased, provided a normally-used transmitted sound pressure is adopted. However, it has been found that that is not true in cases where the transmitted sound pressure is larger. In such case, the microbubbles which have flowed into a diagnostic region vanish instantaneously, with the result echo signals will be extremely low in intensity. The transmitted sound pressure and the number of residual microbubbles in a diagnostic region are qualitatively related to each other, as shown in FIG. 3.

The transmitting condition controller 31 operates as shown in FIG. 2. where it is first determined whether or not the control of transmitted sound pressure is initiated (FIG. 2, step 101). This determination is performed by making the controller 31 detect if the execution button 13D installed on the operation panel 13 has been operated or not. When this determination is YES (i.e., the start of the control), the controller 31 receives an beam-formed echo signal $S_{echo}$ from the receiver 23, and set its signal value (intensity) as Sa (step 102). The value Sa of the echo signal $S_{echo}$ read herein is, for example, an integrated value over an entire image to be displayed.

The controller 31 then provides the transmitting unit 21 a sound pressure control signal $S_{sd}$ for decreasing the transmitted sound pressure by a predetermined value ΔD (step 103). In response to this Bound pressure signal $S_{sd}$, the transmitting unit 21 decreases the drive voltage outputted by the pulsers by a value corresponding to the decremented value of the sound pressure. As a result, the sound pressure in a field in a diagnostic region which has been irradiated from the probe 11, is decreased by a specified value ΔD. Under the decreased sound pressure, an echoed ultrasound signal is received by the probe 11, then its reception signal converted into the electric quantity is processed in the receiving unit 22, before being formed into an echo signal by the receiver 23.

The echo signal $S_{echo}$ read again by the transmitting condition controller 31, where its signal value is regarded as Sb (step 104). When the echo signal $S_{echo}$ which has been produced under the decreased sound pressure is received, the percentage of crush of the microbubbles is suppressed or at least unchanged, as understood from FIG. 3. In consequence, the echoed ultrasound signal is increased in intensity depending on the suppression against the crush, or, decreased in intensity depending on the lowered sound pressure. The echo signal is therefore increased or decreased in value (in some cases, its value may be unchanged).

The transmitting condition controller 31 then determines if Sa>Sb is established or not using the signal values Sa and Sb stored therein so far (step 105). If NO at this determination, that is, Sa≦Sb has been realized, the recognition is that the transmitted sound pressure has not reached its optimum value. In this case, the signal value Sa produced before the reduction is substituted for the signal value Sb produced after the reduction (step 106). Then the processing is returned to step 103. Thus the transmitted sound pressure is again decreased by the given value ΔD, and the determination of if Sa>Sb has been established or not is performed, like the above (steps 103 to 105). A series of these steps are repeatedly performed until Sa>Sb is established.

When the sound pressure has already reached to a level at which microbubbles are no longer vanished (crushed) in the forgoing processing including the sound pressure reduction and the signal comparison, the echo signal intensity will decrease at the next reduction in the sound pressure. When such situation is realized, the determination at step 105 becomes Sa>Sb (YES) for the first time. This means that the sound pressure transmitted at the time when Sa>Sb has been determined is an optimum sound pressure for transmission. In the end, the sound pressure recognized as the optimum value is memorized (step 107), terminating the processing.

In this way, the manual operation of the execution button 13D on the operation panel 13 by an operator allows transmitted sound pressure to be automatically controlled to its optimum value under ECG gating. Responsively to the injection of a contrast medium into a patient, the optimization control can be started by hand. The start timing can be set easily at any time when an operator desires, such as in the beginning of screening. This manual control configuration can give an operator choice about performing the optimization control.

A sound pressure brought by an ultrasound beam signal which has undergone the above optimization control hardly vanish microbubbles flowing into a diagnostic region, providing the echo signals the highest intensities, and raising the effect of contrast imaging. Particularly, even if an organ parenchyma where blood flows slowly or a diagnostic region including relatively thin blood vessels run is imaged, a situation that microbubbles flowing into a diagnostic region are crushed in turn due to the irradiation of ultrasound waves before obtaining the effect of contrast imaging, like the conventional one, can be avoided steadily.

Therefore, performing the contrast echo imaging under the optimized sound pressure for transmission leads to acquiring the echo signal whose signal to noise ratio is higher than the conventional one. Resultantly, there can be obtained B-made images or color blood flow images made by superposing CFM-mode images on B-mode images, in which the effect of intensified luminance of the echo signals is fully exhibited by a contrast medium.

In the foregoing processing comparing the echo signal values Sa and Sb to each other, the echo signal responsible for this comparison is not limited to the forgoing embodiment where the echo signal used is an integrated value over the rasters existing in an entire image. Alternatively, it is possible that the echo signal is produced for only representative transmitting rasters (for example, five rasters in the central region of an image), thereby lowering an amount of calculation. Alternatively, the echo signal may be produced for only rasters residing within a region of interest on an image designated by an operator. According to this ROI setting, a local region which seems to be clinically important can be specified, and an optimum transmitting condition to the local region can be set automatically, remarkably increasing accuracy in the optimum control.

Second Embodiment

Figure 4:
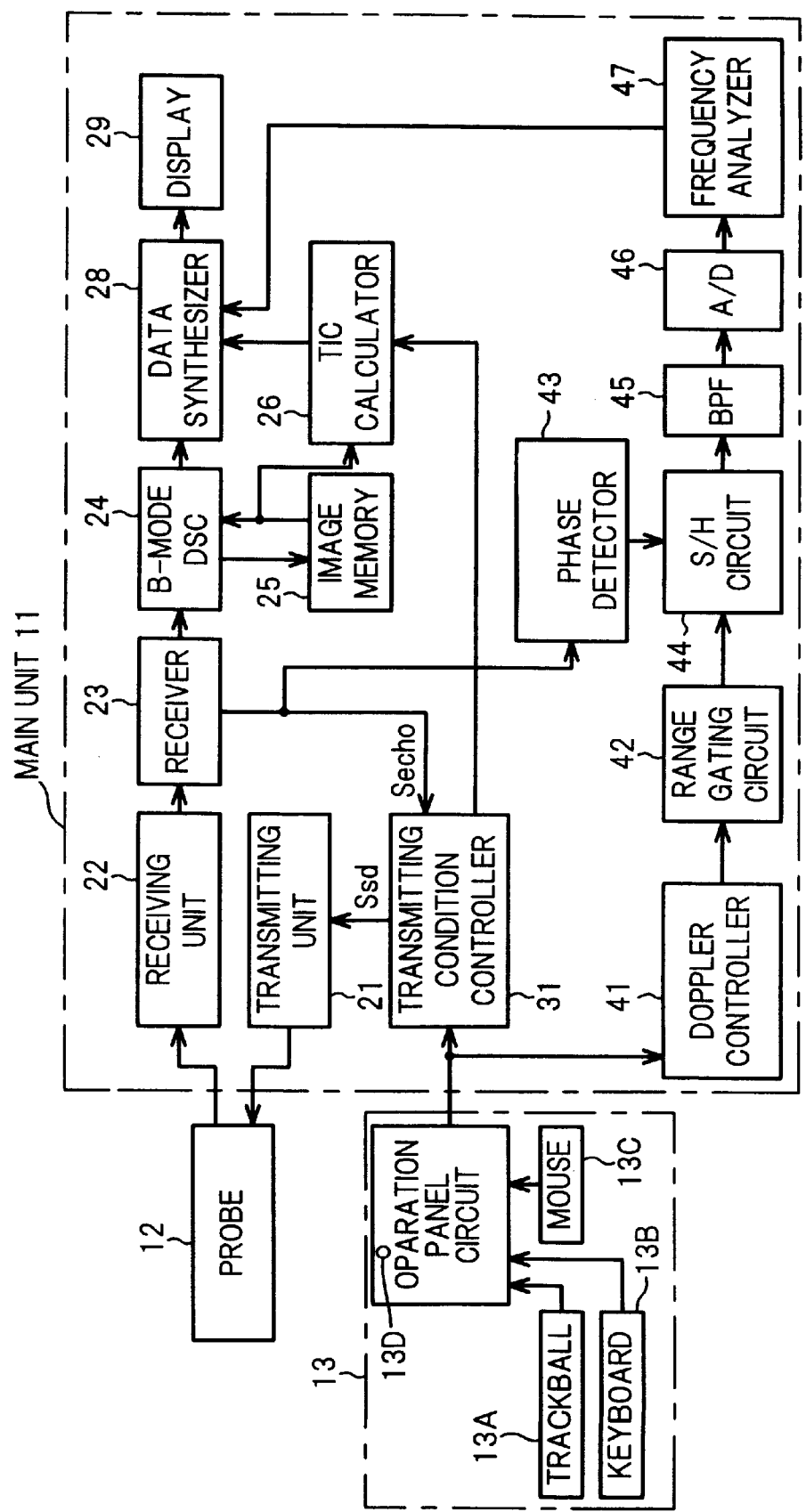
FIG. 4 is a block diagram showing a diagnostic ultrasound apparatus according to a second embodiment of the present invention.

Referring to FIG. 4, a diagnostic ultrasound apparatus according to a second embodiment of the present invention will be described. In this apparatus, the foregoing optimum control of transmitting conditions is applied to pulsed wave Doppler imaging.

The diagnostic ultrasound apparatus schematically shown in FIG. 4 comprises circuitry for a PWD-mode in place of the Doppler unit for a CFM-mode arranged in FIG. 1 but the circuitry for an ECG system and the external outputting unit are omitted from the apparatus.

The PWD-mode circuitry includes a Doppler controller 41 coupled with the operation panel 13, as well as a range gating circuit 42, phase detector 43, sample/hold circuit 44, BPF 45, A/D converter 46, and frequency analyzer 47 which are arranged in this order at the output stage of the controller 41. The phase detector 43 receives an beam-formed echo signal form the receiver 23, like the transmitting condition controller 31.

An operator uses the operation panel 13 to place a sample volume at part of a displayed tomographic image with a cross-mark ROI or others. In response to this placing, positional information specifying a volume region is supplied to the controller 41.

The controller 41 supplies the range gating circuit 42 a positional signal corresponding to the positional information. The range gating circuit 42 generates a range gating signal which corresponds to the specified sample volume to send it to the sample/hold circuit 44. In the circuit 44, a signal corresponding to only the specified sample volume is sampled partly from the phase-detected signal supplied from the detector 43. The sampled signal is filtered by the BPF 45, with its lower and higher frequency noise components cut off, and then converted into a digital form by the A/D converter 46, being sent to the frequency analyzer 47. This configuration allows the frequency analyzer 47 to receive at a moment only a signal acquired from a specified sample volume. The analyzer 47 frequency-analyzes a train of phase-detected data acquired from the specified sample volume, providing the data synthesizer 28 spectrum data changing from time to time. Thus, together with a B-mode tomographic image, Doppler information acquired from a specified sample volume is visualized as a spectrum.

On one hand, like the first embodiment, the transmitting condition controller 31 is able to perform the forgoing optimization control of transmitting conditions, such as transmitted sound pressure, in response to the operator's operation to the execution button 13D at proper times.

Therefore, as to the PWD-mode scanning, in the same manner as in the first embodiment, transmitting conditions can be optimized accurately. Particularly, since only a signal acquired from a specified sample volume is given to the frequency analyzer at a moment in this PWD-mode imaging, such optimization control is extremely effective.

Third Embodiment

Figure 5:
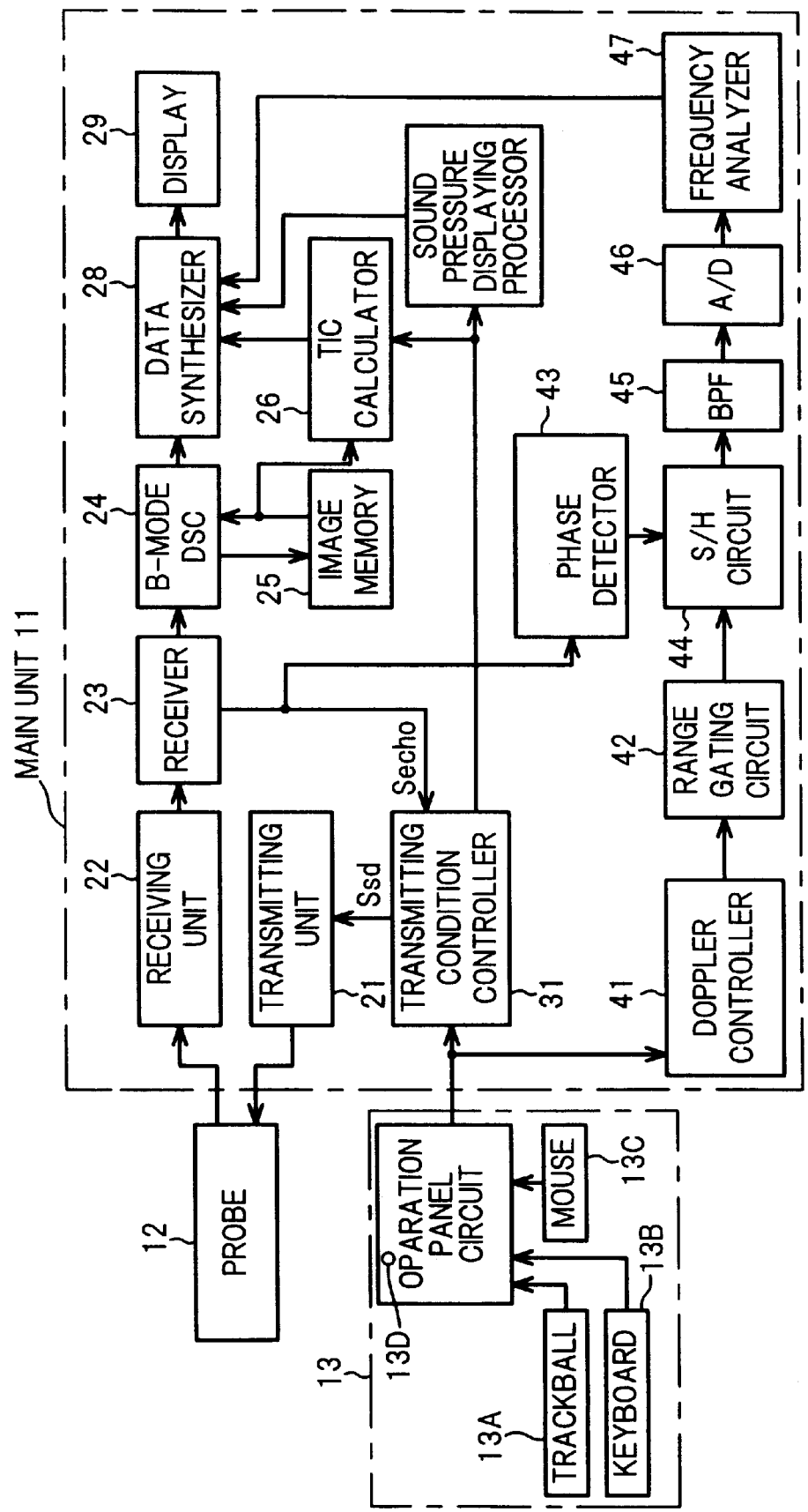
FIG. 5 is a block diagram showing a diagnostic ultrasound apparatus according to a third embodiment of the present invention.

Referring to FIGS. 5 to 6, a third embodiment of the present invention will be described. This embodiment concerns display of transmitted sound pressure (i.e., power value) which is subjected to optimization control.

A diagnostic ultrasound apparatus shown in FIG. 5 comprises, in addition to the same components shown in FIG. 4, a sound-pressure displaying processor 51 inserted between the transmitting condition controller 31 and the displaying data synthesizer 28. The sound-pressure displaying processor 51 includes a CPU as its main component, for example. The processor 51 not merely reads in real time transmitted sound pressures controlled in the controller 31 but also sends to the synthesizer 28 numerical data and/or graphical data indicative of the transmitted sound pressure which is automatic-controlled in real time. Accordingly, changes in the sound pressures controlled in the process of optimization thereof and a finally adjusted optimum pressure can be observed at a glance.

Figures 6A, 6B:
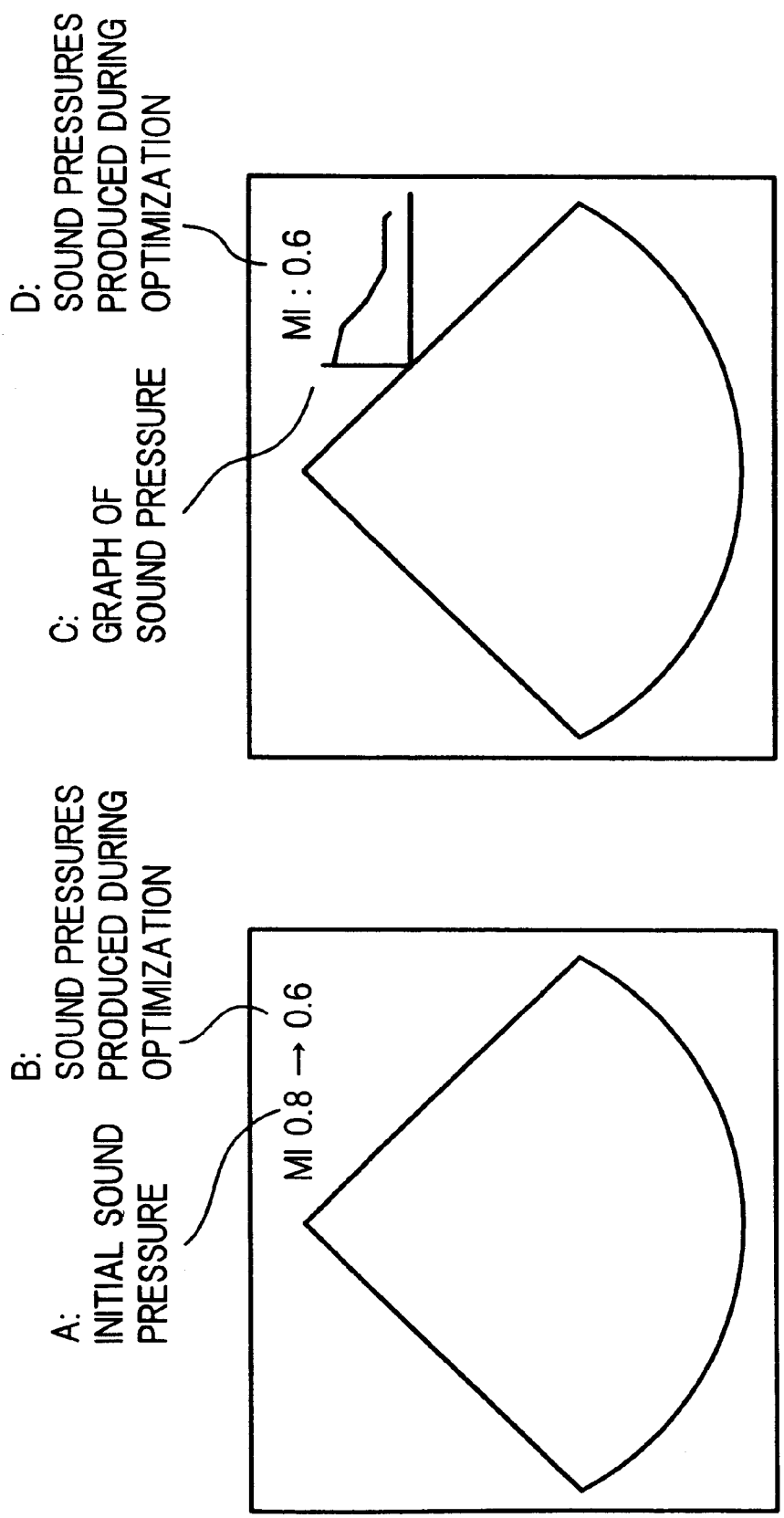
FIGS. 6A and 6B show examples displayed concerning transmitted sound pressure.

Display examples of the transmitted sound pressure, which are performed by the displaying processor 51, are shown in FIGS. 6A and 6B, respectively. In the case of FIG. 6A, an initial value A of the sound pressure is displayed at the upper right corner in an image, while sound pressure values B produced during the optimization control, which changes from the initial value A to another value in turn, are pointed through an arrow at the right side of the initial value A and updated and displayed thereat in real time. On one hand, FIG. 6B displays together at the upper right corner in an image both a graph C which represents temporal changes in transmitted sound pressure values from its initial value and sound pressures values D which change in real time during the optimization control.

Such display helps an operator understand clearly and steadily changes in controlled sound pressures from the beginning and also a present sound pressure which has been lowered, contributing to smoothing manual operation.

The display modes described herein may be applied to the forgoing first embodiment.

Fourth Embodiment

Figure 7:
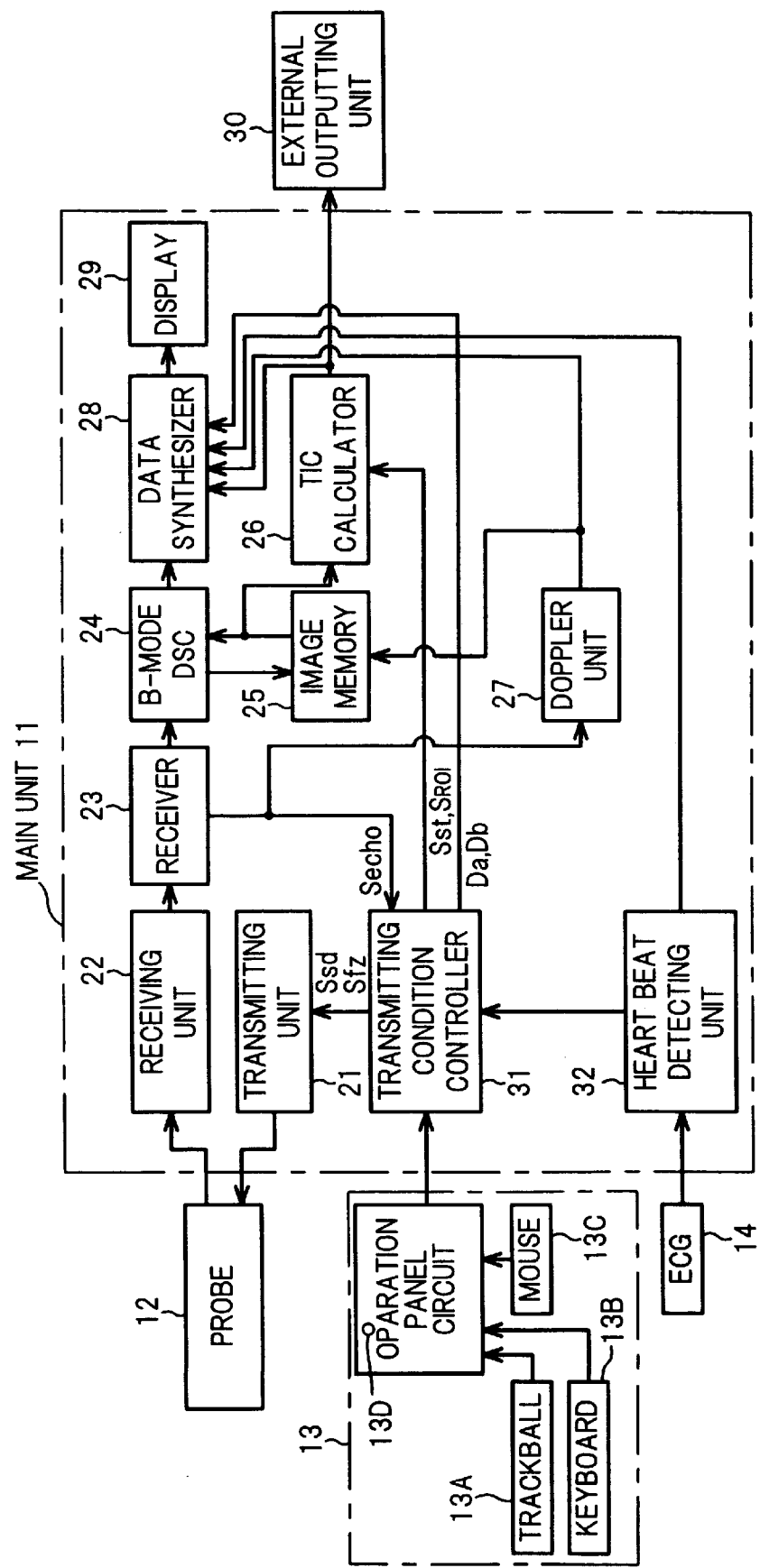
FIG. 7 is a block diagram showing a diagnostic ultrasound apparatus according to a fourth embodiment of the present invention.
Figure 8:
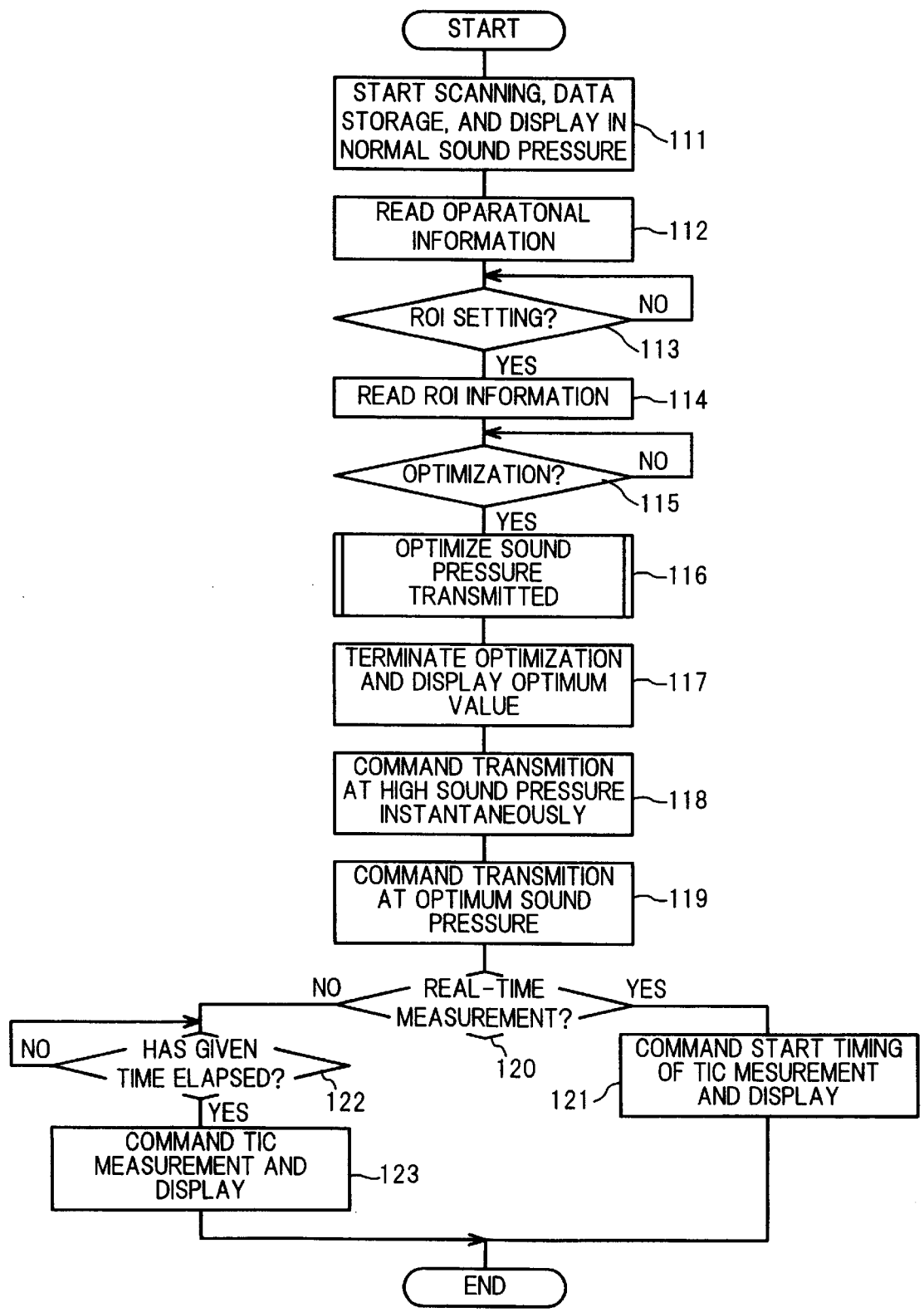
FIG. 8 is a flowchart schematically showing a control example executed in a transmitting condition controller.

Referring to FIGS. 7 to 8, a fourth embodiment of the present invention will be described. The embodiment is concerned with a combination of optimization of transmitted sound pressure and TIC measurement. Preferably, an ultrasound contrast medium is injected with sustaining injection in this embodiment.

As described before, in the case that the TIC measurement performed together with the contrast echo imaging is based on intensified luminance brought about by a contrast medium flowing into a region of interest, essential parameters include a peak value in changes of luminance levels, a luminance increasing speed, and washing out from the peak luminance. In performing the TIC measurement for such parameters which concentrates on measurement of temporal changes, if the foregoing optimization of transmitted sound pressure is performed, there poses a problem that information about changes in luminance (or its precise information) is not provided for a period for the optimization control. Therefore, a diagnostic ultrasound apparatus of this embodiment aims at avoiding such an unfavorable situation and enabling accurate, stable TIC measurement, additionally to the objects of the present invention.

A diagnostic ultrasound apparatus shown in FIG. 7 comprises the transmitting condition controller 31 that executes processing illustrated in FIG. 8 in order to control the TIC calculator 26 in terms of its calculation start timing and display associated with the end of optimization. The remaining components are the same or similar as or to those in the first embodiment in FIG. 1.

As shown in FIG. 8, the transmitting condition controller 31 first commands ultrasound beam scanning based on a normal sound pressure employed as an initial value, storing echo data into the image memory 24 for each frame, and display on the display 29 (step 111). As a result of it, using echo signals acquired on the normal transmitted sound pressure which has been used conventionally, display of color blood flow images in which a CFM image is superposed on a B-mode image are commenced on the display 29. These scanning, storing of echo data, updating of images are continued at intervals in real time except for freezing the image.

The controller 31 reads information about operation from the operation panel 13, and it obtains information indicating if TIC measurement should be performed in a real-time scanning state or in an image-frozen state (step 112). Furthermore, it is determined if a graphical region of interest (ROI) is placed by an operator at any location on the displayed color image (step 113). When the ROI has been placed, information concerning a ROI position, a ROI size, and others are read (step 114).

The controller 31 then executes steps 115 to 120 in sequence. First whether the optimization of transmitted sound pressure adopted as one transmitting condition is commenced or not is determined on information form the execution button 13D (step 115). When the affirmative determination is recognized, the optimization control is performed (step 116), which is done with the similar processing to steps 102 to 107 in FIG. 2. This processing automatically sets an optimum sound pressure transmitted, by which echo signals each having a maximum intensity are emanated from microbubbles. After completing the optimization, the controller 31 then sends to the displaying data synthesizer 28 data Da indicative of the completion and data about an optimized sound pressure (step 117). By this data sending, a mark notifying the completion of the optimization and numerical data showing the optimized sound pressure are displayed at part of the screen of the display 29.

The controller 31 commands the transmitting unit 21 to instantaneously transmitting an ultrasound beam signal of a sound pressure as high as to crush all the microbubbles existing on the beam paths. This transmission causes almost all the microbubbles residing in a scanned volume and its slight neighborhood to be crushed (vanished) instantaneously.

After this raised sound pressure, the controller 31 immediately commands the transmitting unit 21 to return the sound pressure to the optimum one which has been already set and keep the transmission at the optimum one (step 119). Therefore, after the instantaneous crush of the microbubbles residing in the scanned plane-like volume and its neighborhood, on account of returning the sound pressure, new microbubbles flow into a vacant plane-like volume in which the microbubbles have not existed for an instant. Since the microbubbles newly flowed are subjected to the optimum sound pressure, their crush rates are less, generating again an echo signal of a maximum intensity.

Based on the information read at step 112, the controller 31 then determines whether or not the TIC measurement is performed in a real-time sate or an image-frozen state. If the determination falls into the real time measurement (YES), the processing proceeds to step 121, where a start timing signal $S_{st}$ allowing the TIC measurement to be displayed and the measured results to be displayed as well as ROI information $S_{ROI}$ (its position and size) are sent to the TIC calculator 26. In response to the signal $S_{st}$, the TIC calculator 26 reads out frame by frame the echo data stored in a time-sequence basis in the image memory 25 through the B-mode DSC 24, and calculates various parameters specified from the echo data within the specified ROI. The calculated results of the parameters are sent to the display 28 and the external outputting unit 30, with the result that real-time color blood flow tomographic images and a graph and/or numerical data representing the TIC measurement results are displayed on the display 29 in, for example, a divided display form in almost real time.

On the contrary, the determination that the TIC measurement is performed in the image-frozen state at step 120 (i.e., NO thereat), the processing proceeds to step 122, where the scanning state according to the current optimum sound pressure is ordered to be continued for a certain interval. The interval is defined to acquire necessary echo data for desired TIC measurement. During the interval, echo data are acquired by the specified number of frames and stored in the image memory 25. When the interval has elapsed, the controller 31 sends out the start timing signal $S_{st}$ and ROI information $S_{ROI}$ to the TIC calculator 26, like the forgoing step 121, and concurrently sends out a freezing signal $S_{fz}$ to the transmitting unit 21. This freezing command causes the displayed tomographic image on the display 29 to be frozen. Moreover, the TIC calculator 26 reads a plurality of frames of echo data which have been stored in the image memory 25 during the acquisition interval, and calculates the specified various parameters from the echo data within the specified ROI. The calculated results are sent to both the data synthesizer 28 and the external outputting unit 30. As a result of it, a frozen color blood flow tomographic images and a graph and/or numerical data representing the TIC measurement results are displayed on the display 29 in, for example, a divided display form.

According to this embodiment, the transmitted sound pressure is instantaneously-raised in intensity to instantaneously crush (vanish) almost all microbubbles which exist in a scanned plane-like volume, and than returned promptly to an optimum sound pressure. Therefore, it is possible to observe the behaviors of microbubbles which flow in a totally vacant space, providing observation equivalent to the beginning of contrast echo imaging. TIC measurement succeeding to the instantaneously-raised sound pressure, which is performed in the real-time or frozen state, becomes accurate and stable.

In other words, the fact that information about changes in luminance levels due to a contrast medium was unavailable or its accuracy was deteriorated during the optimization of transmitted sound pressure is completely avoided. Additionally the start timing of TIC measurement is properly controlled, so that it is also steadily prevented that echo data received during the optimization control penetrates into TIC measurement or affects it.

In this apparatus, the TIC measurement mode can be selected from the real-time display mode and the image-frozen mode, thus widening the measurement.

Still, a series of operations including the ROI setting for TIC measurement, the optimization control of transmitted sound pressure, the scanning at an optimum sound pressure, and the TIC measurement are automated. This relieves operation work, increase efficiency in operation, and raises a patient throughput. The ROI setting may be designed to be performed for each time of TIC measurement.

Fifth Embodiment

Referring to FIGS. 9 to 12, a fifth embodiment of the present invention will be described. A diagnostic ultrasound apparatus of this embodiment features obtaining images which represent inflow amounts of blood flow utilizing physical properties of an ultrasound contrast medium. This image data acquisition uses a technique referred to as flash echo imaging described before. In the flash echo imaging, an ultrasound beam is transmitted intermittently so that microbubbles accumulate in a scanned plane-like volume during intervals with no irradiation, and are crushed at a time by the next irradiation of an ultrasound beam, thus generating echo signals of higher intensities. Unlike the foregoing embodiments, the present embodiment uses a different technique that crushes deliberately microbubbles under given interval rules, efficiently providing images. In this embodiment, an ultrasound contrast medium is injected with the sustaining injection method and contrast echo imaging is performed with the contrast medium.

Figure 9:
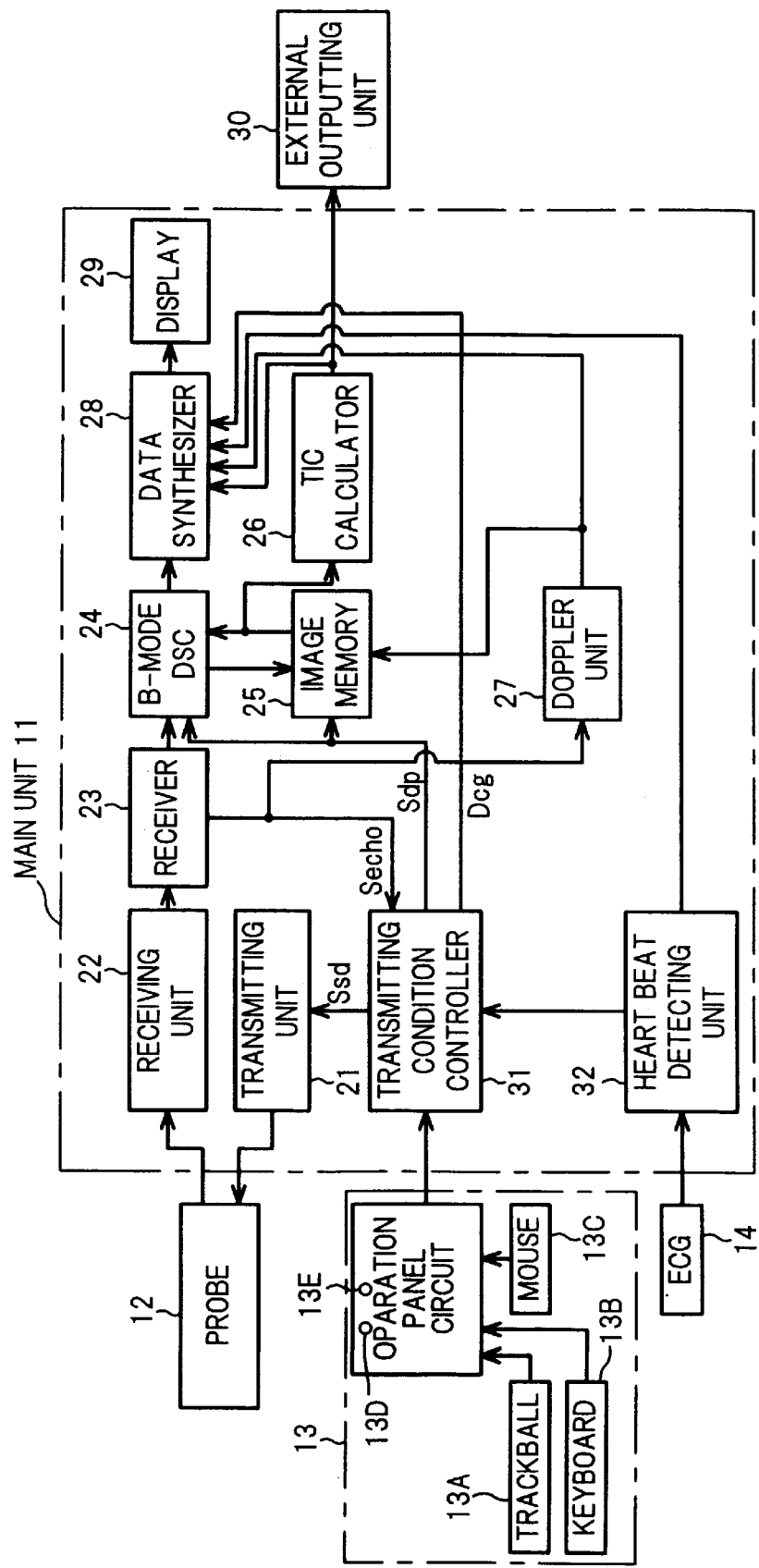
FIG. 9 is a block diagram showing a diagnostic ultrasound apparatus according to a fifth embodiment of the present invention.

FIG. 9 shows a diagnostic ultrasound apparatus performing the contrast echo imaging. The transmitting condition controller 31 controls a frame rate for transmission and further sends a command for loop-redisplay of images to the B-mode DSC 24 and the image memory 25. The operation panel 13 has a freezing button 13E. The remaining components and their operations are the same or similar as or to those in FIG. 1.

Figure 10A:
FIG. 10A is a sequence chart showing an example of controlling frame intervals according to the conventional technique.
Figure 10B:
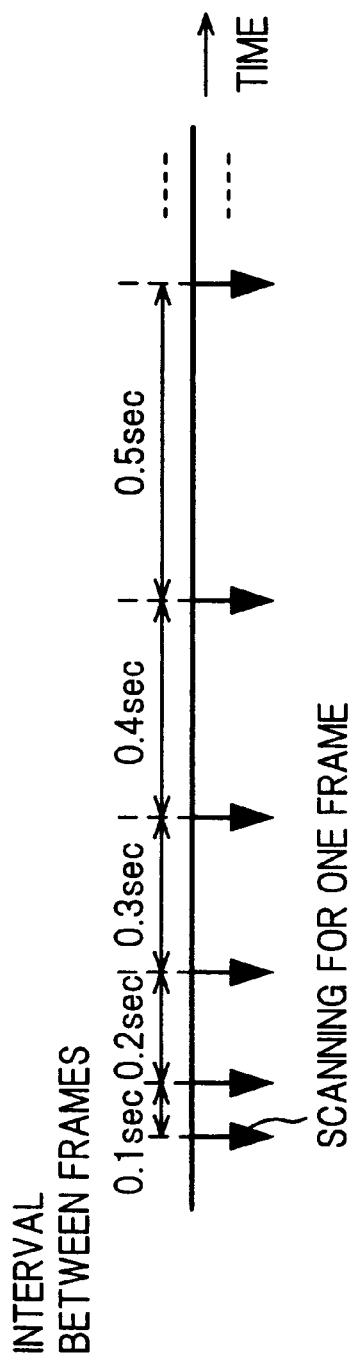
FIG. 10B is a sequence chart showing an example of controlling frame intervals according to the present invention.

In the conventional diagnostic ultrasound apparatus, a frame rate (intervals for transmission) is normally controlled at a certain rate during imaging, as shown in FIG. 10A. The frame rats is changed, of course, when depths of a field of view and densities of ranters are altered, but it is normal that the frame rate is maintained at a constant rate under constant scanning conditions. In contrast, in the embodiment, even in constant scanning conditions, the transmitting condition controller 31 alters the frame rate, as illustrated in FIG. 10B. In this case, the frame rate is set such that it becomes longer time-sequentially, such as 0.1 sec., 0.2 sec., 0.3 sec., ..., 1.0 sec., which is preset in a program executed by the CPU.

The frame rate can be set in the opposite way; that is, it becomes shorter time-sequentially. The sequence shown in FIG. 10B can be repeated in the case of injecting a contrast medium with the sustaining injection method.

Figure 11A:
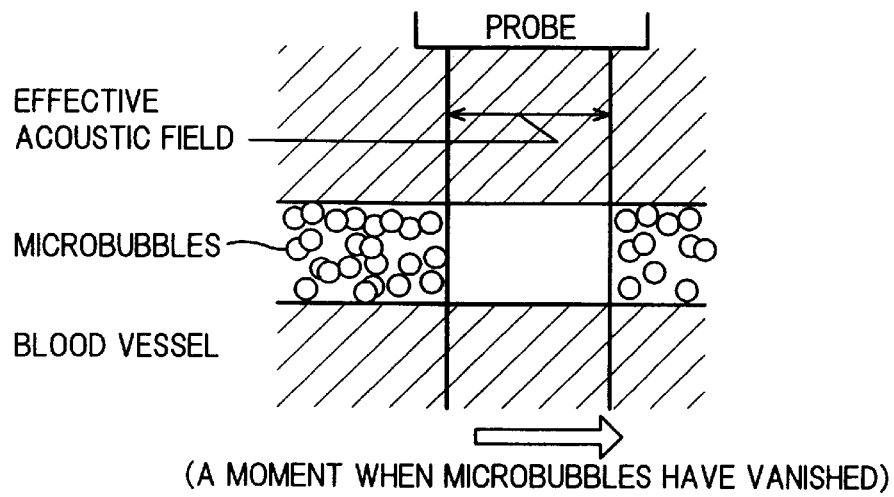
FIGS. 11A to 11C are illustrations each showing the relation between frame intervals and the collapse of microbubbles.
Figure 11B:
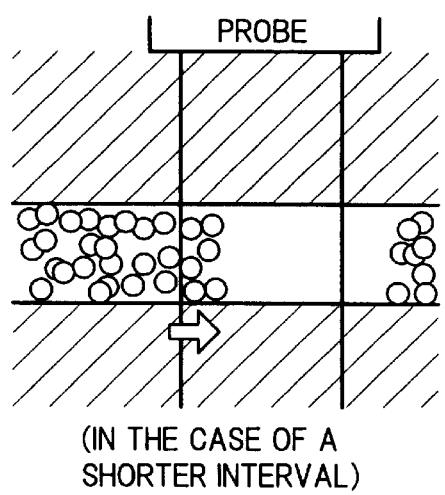
Figure 11C:
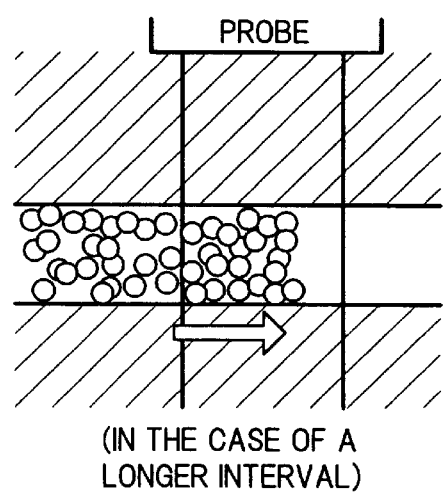

A principle that images representing amounts of blood flow are obtained by changing the frame rate will be described below. FIG. 11A pictorially shows an instantaneous state where microbubbles existing in an effective acoustic field intersecting a blood vessel have vanished due to irradiation of ultrasound waves. After this vanishing, new microbubbles begin to inflow into the acoustic field immediately. In the case that the next irradiation is carried out in a relatively shorter time, only a small amount of microbubbles has inflowed into the field and stayed there, as shown in FIG. 11B. If the flash echo imaging is performed in this state, an echo signal is generated with a lower intensity, due to a small amount of microbubbles. However, when the frame rate (intervals for transmission) becomes longer, as shown in FIG. 11C, amounts of microbubbles are proportionally on the increase, thus generating echo signals with higher intensities.

When taking a time required to fulfill the effective acoustic field with microbubbles as a saturation time $T_{full}$, scanning at longer intervals (i.e., frame rates) longer than the saturation time $T_{full}$ generates only echo signals having a constant intensity.

Figure 12:
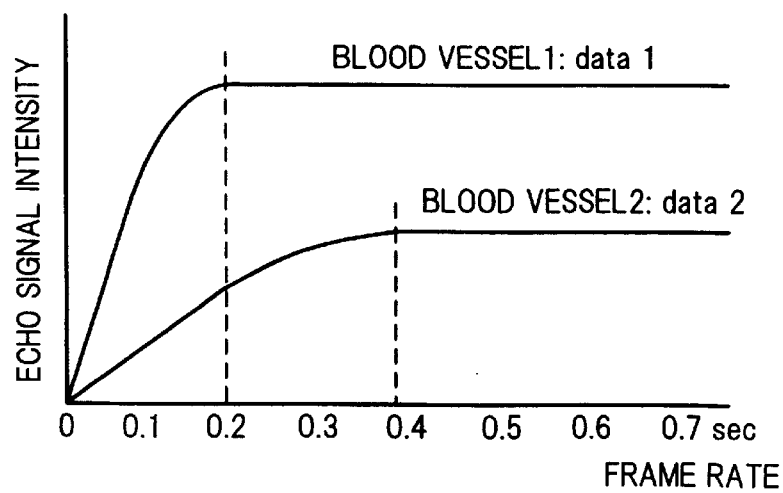
FIG. 12 shows graphs explaining qualitative relation between frame intervals and echo signal intensities.

This relation is qualitatively exemplified in FIG. 12, where the lateral axis is assigned to the frame rate and the longitudinal axis to the echo signal intensity. In this figure, two blood vessels 1 and 2 (data 1 and data 2) are shown and compared to each other. The saturation time $T_{full}$ of one blood vessel 1 is 0.2 sec., and that of the other blood vessel 2 is 0.4 sec. These two curves show that since the blood vessel 1 is faster in the blood supplying speed and higher in the signal intensity than the blood vessel 2, the blood vessel 1 carries a greater deal of amount of blood than the blood vessel 2.

On the basis of such principle, the transmitting condition controller 31 controls the frame rate in compliance with a sequence shown in FIG. 10B, for example. A plurality of frames of image data (B-mode and CFM-mode image data) on the sequence are stored in the image memory 25. On completion of a series of transmission processes, the controller 31 responses to an operator's command from the freezing button 13E to stop the scanning, before sends to the image memory 25 and the DSC 24 a signal $S_{dp}$ for loop redisplay. In consequence, loop-redisplayed on the display 29 is a B-mode tomographic image, or, a superposition image of a color blood flow image onto a B-mode image, of which luminance levels are gradually on the increase. The larger the blood flow amount, the higher its luminance is as well as the faster it runs. These differences can be used to distinguish and measure amounts of blood flow.

The transmitting condition controller 31 is configured to provide the data synthesizer 28 data $D_{og}$ including numerical data indicative of the sequence shown in FIG. 10B (that is, intervals corresponding to periods for accumulating microbubbles) or various necessary graphical data. As a result, on the loop-redisplayed image, information about these intervals is reproduced and displayed together. This display manner also provides an operator indispensable information in understanding amounts of blood flows, making it possible to improve efficiency in diagnosis.

Figure 13:
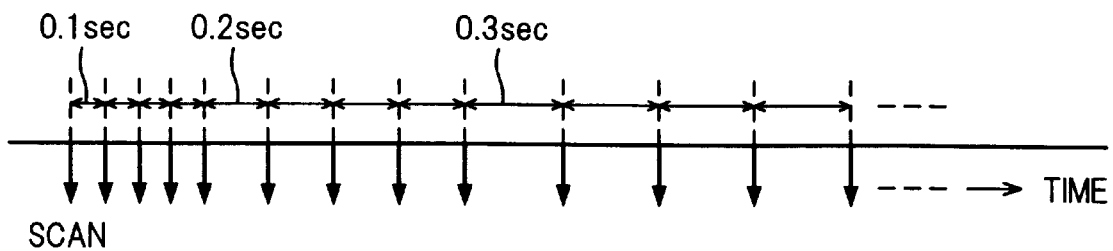
FIG. 13 shows a variant explaining another example of frame intervals.

An alternative example of the fifth embodiment will be described. When considering display performance for amounts of blood flow, although it is essential that the frame rate be altered under predetermined rules, changes in the intervals, in themselves, can be in accordance with any function. For example, as shown in FIG. 13, the frame rate can be set controlled to a sequence where the same intervals are repeated a plurality of times and getting larger gradually, such as 0.1 sec., 0.1 sec., 0.1 sec., 0.1 sec., 0.2 sec., 0.2 sec., 0.2 sec., 0.2 sec., etc. The resultant plural-frame images are subjected to averaging of pixel values pixel by pixel so that a single image consisting of the averaged pixel values is produced and displayed as a representative of a plurality of images acquired at the same intervals.

Figure 14:
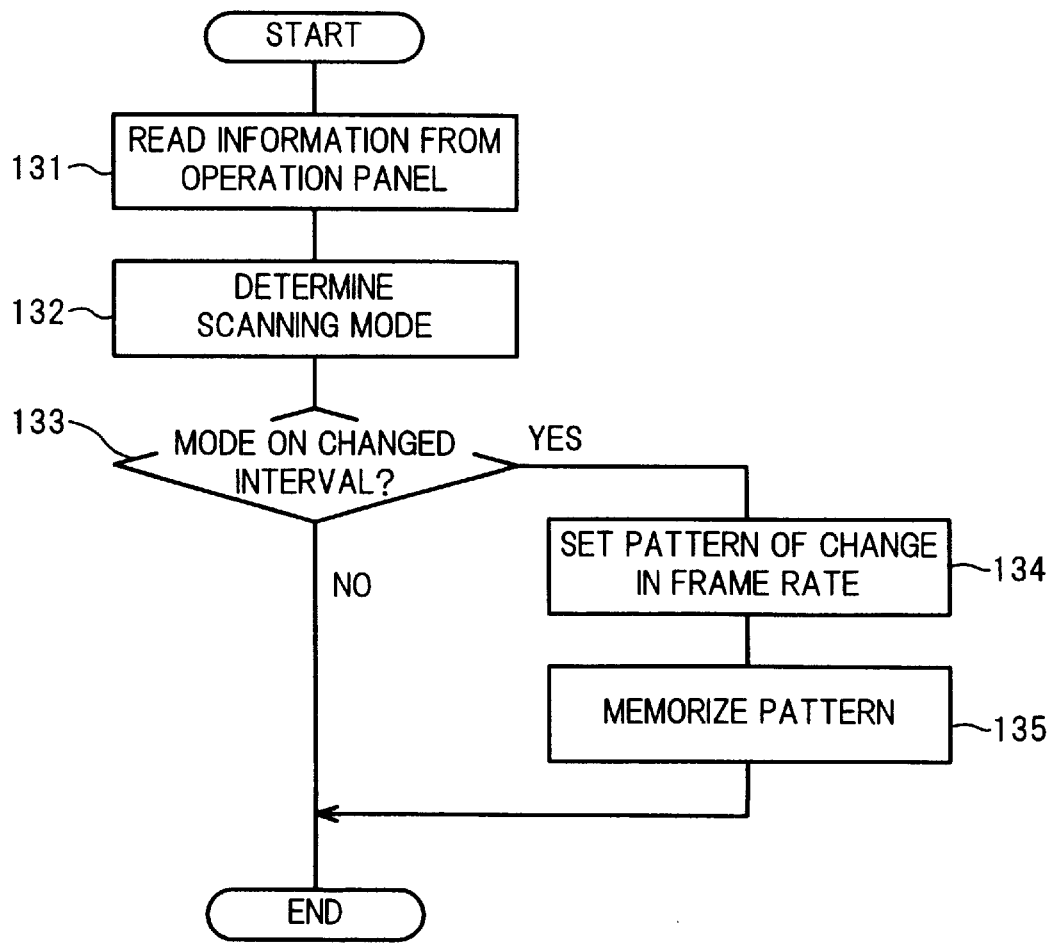
FIG. 14 is a schematic flowchart showing a setting procedure to a scanning mode with which frame intervals are changed.

Another alternative example relates to setting the frame rate. Practically the controller 31 performs processing shown in FIG. 14. The controller 31 reads information from the operation panel 13 to which an operator gives necessary data (step 131), determines a scanning mode described in the fifth embodiment (a mode in which the frame rate is changed deliberately in a certain regularity) (step 132). If such scanning mode has been instructed (YES at step 133), a pattern of changes in frame intervals is set and memorized (step 134, 135). The pattern may be set by an operator, but it is convenient to prepare tables memorizing a plurality of patterns beforehand and display the tables for selection.

Figure 15:
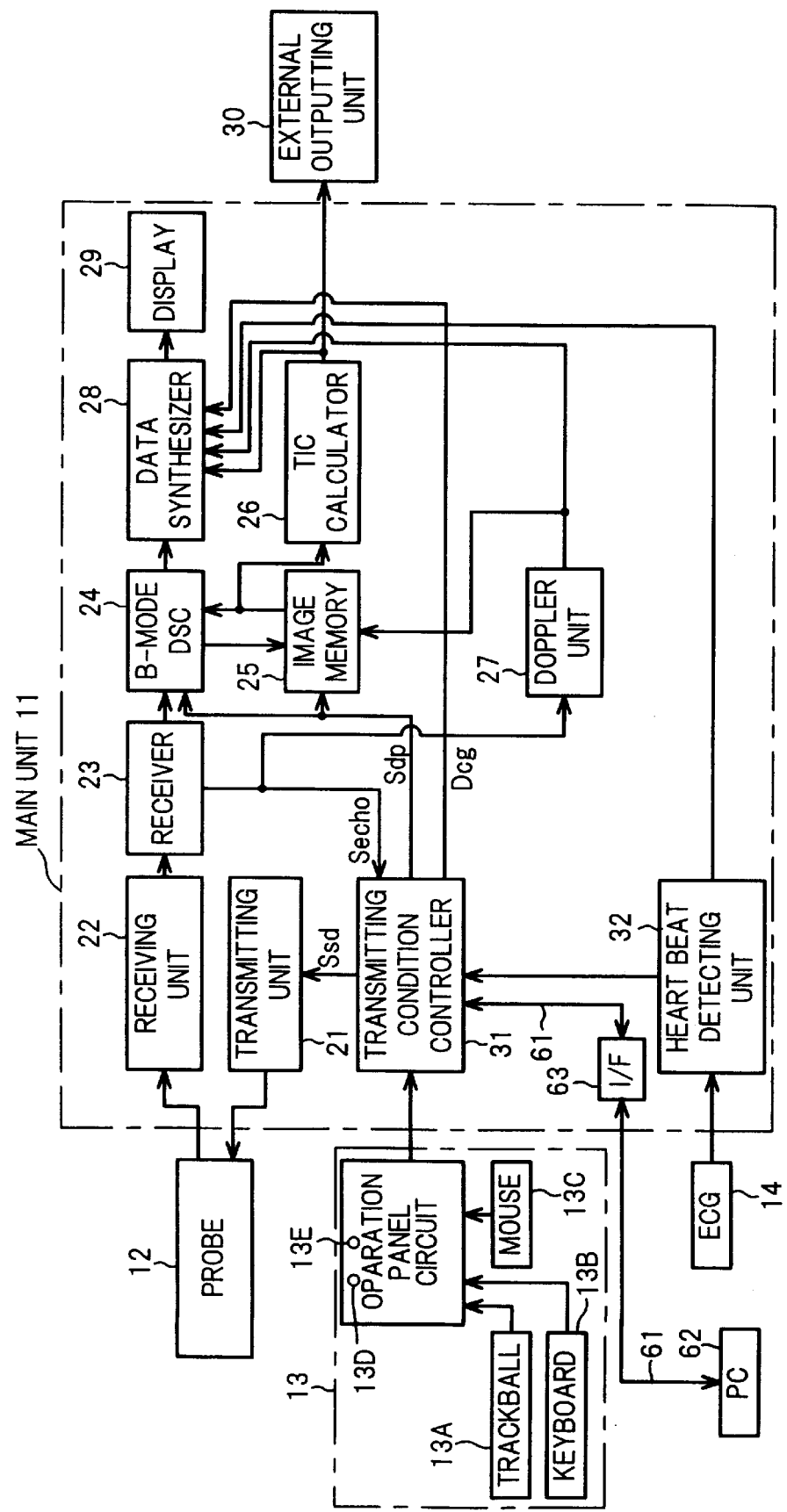
FIG. 15 shows another variant of a diagnostic ultrasound apparatus according to the fifth embodiment.

Another example concerns controlling a pattern of changes in frame intervals from the outside of a diagnostic ultrasound apparatus. FIG. 15 shows one such example for such control. The transmitting condition controller 31 is coupled with a communication line 61 connecting a personal computer 62 via an interface 63 inserted therebetween. The personal computer 62, which is placed outside the apparatus, provides the controller 31 a command for controlling the forgoing pattern.

Sixth Embodiment

Figure 16:
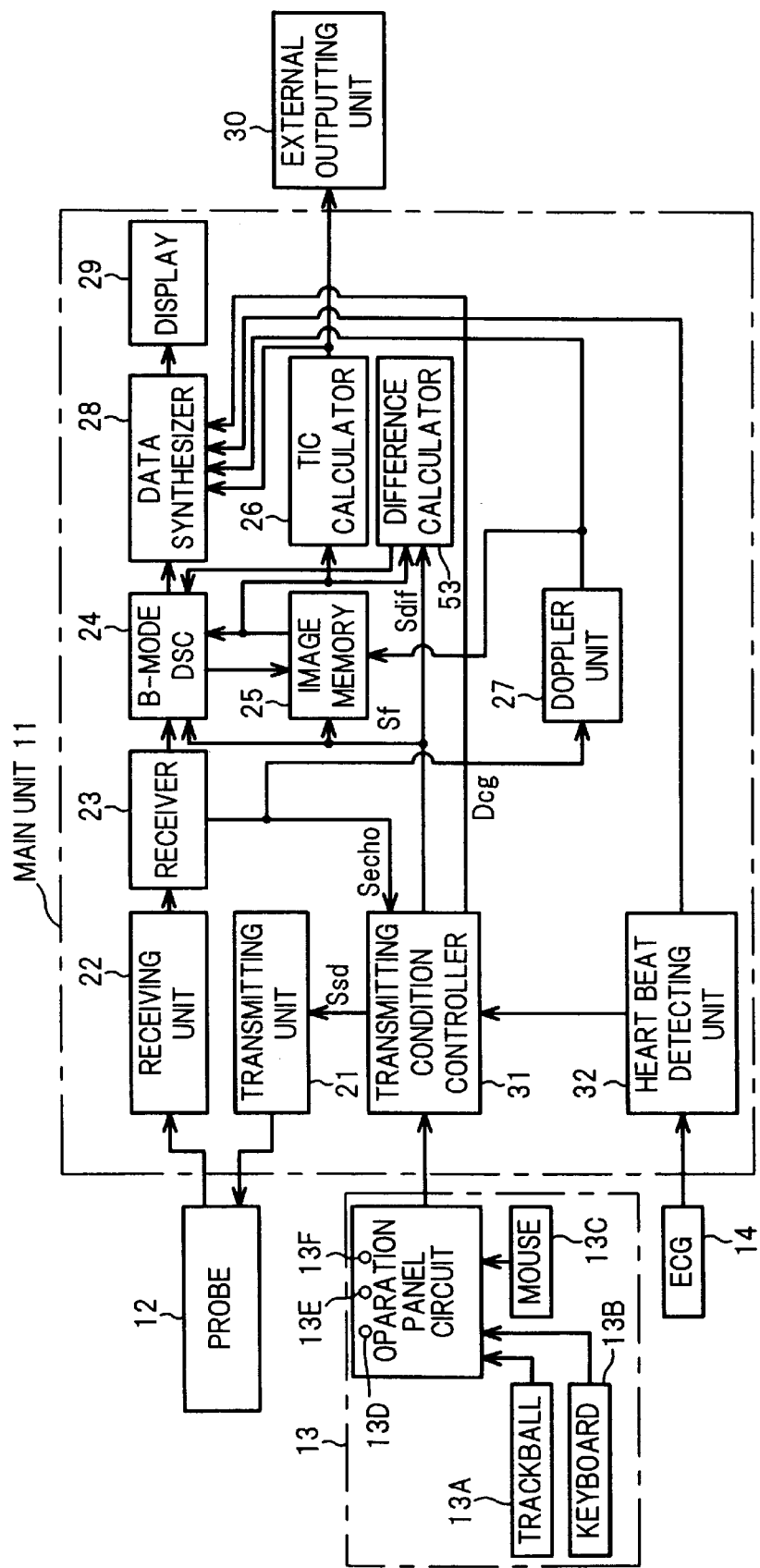
FIG. 16 is a block diagram showing a diagnostic ultrasound apparatus according to a sixth embodiment of the present invention.
Figure 17:
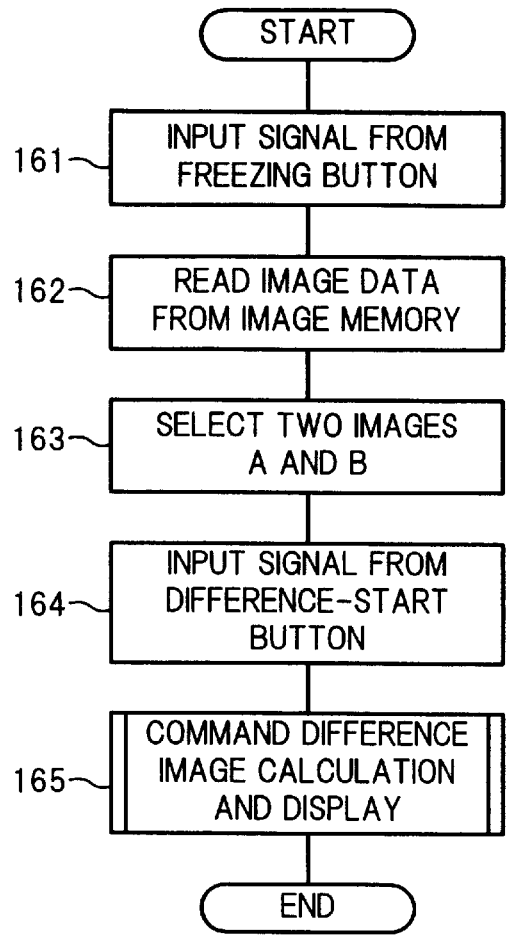
FIG. 17 is a schematic flowchart showing a control example executed in a transmitting condition controller calculating differential images.
Figure 18:
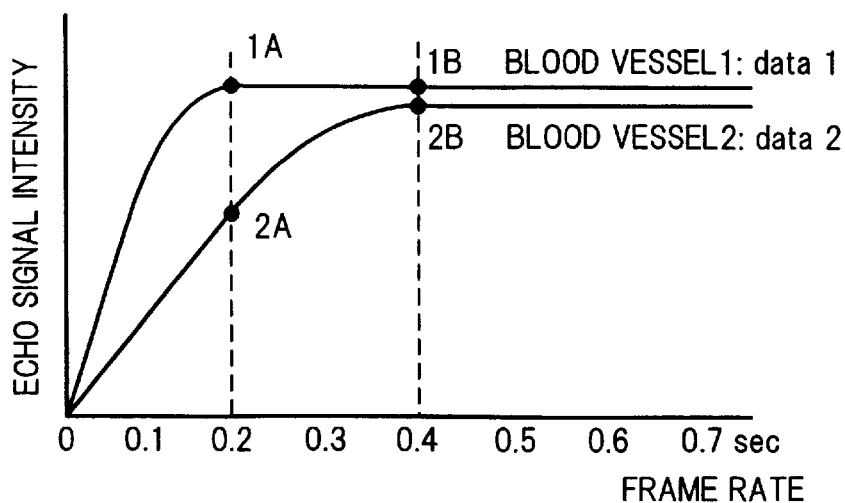
FIG. 18 shows the qualitative relation between frame intervals and echo signal intensities, which explains effects in differential images.

Referring to FIGS. 16 to 18, a sixth embodiment of the present invention will be described. This embodiment features the production of a difference image with respect to amounts of blood flow.

A diagnostic ultrasound apparatus shown in FIG. 16 has a difference calculator 53 which operates on a signal $D_{dif}$ supplied from the transmitting condition controller 31. In response to the signal, the difference calculator 53 reads two frames of image data from the image memory 25, and calculates differences in pixel values between the two frames pixel by pixel. The frame data composed of the differences are subjected to displaying though the B-mode DSC 24. In addition to the freezing button 13E, the operation panel 13 has a difference-start button 13F operated by an operator.

The transmitting condition controller 31 is configured to perform the processing schematically shown in FIG. 17. Echo data are acquired with scanning, before an operator operates the freezing button 13E. When detecting a freezing command from the button 13E (step 161), the controller 31 causes the transmitting unit 21 to stop the scanning, whereas it sends a freezing signal $S_f$ to the DSC 24 and the image memory 25 to multi-display images which have been stored in the image memory 25 (step 162). Using the trackball etc., an operator selects desired two frames of image data A and B for use of difference calculation from the multi-displayed images (step 163). To the multi-displayed images, data showing each image was scanned at what frame rate (i.e., interval for accumulating microbubbles) are also attached.

After this selection, the controller 31 determines whether the difference-start button 13F is operated or not (step 164). When this determination has been done, the controller 31 sends the difference-start signal $S_{dif}$ to the difference calculator 53. The calculator 53 then calculates differences in luminance between the selected images A and B pixel by pixel, and sends calculated difference data to the DSC 24 (step 165). According to this way, after freezing the image, image data which have been recorded in the image memory 25 can be selected at any combination to produce a difference image and can be displayed.

The difference calculation provides an excellent advantage over the conventional imaging. As understood from FIG. 18 where there are shown curves 1 and 2 defined by the frame rate and the echo signal intensity, the curves 1 and 2 for blood vessels will converges on an approximately equal intensity (contrasted luminance), provided that both the curves are extended sufficiently over longer frame rates. In the case of FIG. 18, the approximately equal intensity can be decided to be in a range of over 0.4 sec. in the frame rate. A difference between both the curves lies in the supplying speeds of microbubbles in a range up to 0.4 sec. in the frame rate. If the transmission is carried out based on the flash echo imaging at an interval of 0.2 sec., the blood vessel 1 shows larger contrast effects compared to the blood vessel 2 (refer to points 1A and 2A). Thus, calculating differences between images scanned at an interval 0.4 sec. and an interval of 0.2 sec. provides a difference image, where the pixel values of one blood vessel 1 are canceled and almost zero, due to almost no difference between points 1A and 1B, while the pixels values of the other blood vessel 2 contribute to imaging, because there are enough differences between points 2A and 2B.

After all, performing the difference calculation between two images scanned individually at properly-set different frame rates leads to a unique advantage that blood flow information which is present in a particular range of blood flow speeds can be extracted and displayed, preferably in a loop-redisplay mode.

Concerning the above embodiment, various variations can be added. For example, a plurality of frames of difference image data produced by repeatedly performing the foregoing difference processing can be stored again in the image memory 25 or stored in another memory, and each difference image can be subjected to the calculation of TIC data by the TIC calculator 26. Furthermore, the TIC calculation can be conducted concurrently with the difference calculation.

Another variation is that the forgoing difference calculation is not restricted to post-processing performed in the image-frozen state, but may be performed in real time. For instance, image data obtained almost in real time from the DSC 24 as scanning advances are sent to the difference calculator 53 at predetermined intervals, the difference calculation is immediately conducted on completion of preparing a minimum volume of data necessary for difference calculation, and the difference results are returned to the DSC 24 to be displayed with a tomographic image in, for example, a divisional display mode.

In the foregoing embodiments, a device, such as a personal computer, can be connected with the diagnostic ultrasound apparatus through a communication line, and the device can be configured to control the transmitting unit and others, thus realizing a remote control configuration.

Although the description above contains many specificities, these should not be construed as limiting the scope of the invention but as merely providing illustrations of some of the presently preferred embodiments of this invention. Thus the scope of this invention should be determined by the appended claims and their legal equivalents.

What I claim is:

1. A diagnostic ultrasound apparatus using an ultrasound pulse signal transmitted into a subject to be diagnosed in a transmitting condition, the apparatus comprising:

means for transmitting an ultrasound pulse signal, a plurality of times, into the subject as the transmitting condition is controlled to have different amounts of transmission power;

means for receiving, at each time of the transmission, from the subject, an echoed component of the transmitted ultrasound pulse signal to produce a reception signal; and means for determining an optimum amount of the transmission power defined by the transmitting condition based on the reception signal produced at each time of the transmission.

2. The apparatus of claim 1, wherein the echoed component includes a component of the ultrasound pulse signal echoed by an ultrasound contrast medium of which a substantial constituent is made up of micro-bubbles, the medium being injected into the subject.

3. The apparatus of claim 2, wherein the transmitting means has an ultrasound probe firing the ultrasound pulse signal and the transmitting condition is composed of a parameter to control the transmission power obtained by the ultrasound pulse signal fired by the probe.

4. The apparatus of claim 3, wherein the parameter is one of a driving voltage applied to the probe and a number of transmitting transducer elements incorporated in the probe.

5. The apparatus of claim 2, wherein the determining means are means that determine the optimum amount of the transmission power based on the reception signal corresponding to the echoed component collected from an overall region of interest located in a cross section scanned by the ultrasound pulse signal.

6. The apparatus of claim 2, wherein the determining means are means that determine the optimum amount of the transmission power based on the reception signal corresponding to the echoed component collected partly from a region of interest located in a cross section scanned by the ultrasound pulse signal.

7. The apparatus of claim 2, wherein the determining means are means that determine the optimum amount of the transmission power based on the reception signal corresponding to an operator-specified area within a region of interest in a cross section scanned by the ultrasound pulse signal.

8. The apparatus of claim 2, wherein the transmitting and optimizing means operate in a mode acquiring at least one of a B-mode tomographic image, a color flow mapping (CFM) image, and a pulsed Doppler mode image.

9. The apparatus of claim 2, further comprising means for displaying the determined transmission power.

10. The apparatus of claim 9, wherein the displaying means are configured to display a process of the transmission power under the determination in real time.

11. The apparatus of claim 1, wherein the determining means determine an amount of the transmitting power so as to maximize an intensity of the reception signal.

12. A diagnostic ultrasound apparatus using an ultrasound pulse signal transmitted into a subject to be diagnosed in a transmitting condition, an ultrasound contrast medium being injected into the subject, the apparatus comprising:
  means for transmitting the ultrasound pulse signal a plurality of times, into the subject as the transmitting condition is controlled to have different amounts of transmission power;
  means for receiving, at each time of the transmission, from the subject, an echoed component of the transmitted ultrasound pulse signal to produce a reception signal;
  means for determining an optimum amount of the transmission power based on the reception signal produced at each time of the transmission;
  means for controlling the transmitting condition so as to raise an amount of the transmission power from the optimum amount and then to restore the raised amount to the optimum amount; and
  means for measuring data indicative of a time intensity curve (TIC) of the reception signal after the amount of the transmission power has been restored to the optimum amount.

13. The apparatus of claim 12, wherein the measuring means comprises memory means for storing a plurality of frames of image data corresponding to the reception signal and calculating means for calculating the data of the time intensity curve based on the image data stored in the memory means.

14. The apparatus of claim 12, wherein the measuring means comprises reading and calculating means for reading frame by frame image data produced from the reception signal time-sequentially and calculating in real time the data indicative of the time intensity curve.

15. The apparatus of claim 12, further comprising:
  means for producing a tomographic image using the reception signal produced by the receiving means,
  wherein the measuring means comprises means for displaying the tomographic image and means for operator-placing a region of interest on the displayed tomographic image, and
  the calculating means is configured to calculate the data of the time intensity curve from the plurality of frames of image data corresponding in position to the region of interest placed on the tomographic image.

16. A diagnostic ultrasound apparatus using an ultrasound pulse signal transmitted into a subject to be diagnosed, comprising:
  means for transmitting the ultrasound pulse signal into a same portion of the subject at a transmission frame rate;
  means for changing the transmission frame rate time-sequentially in a same imaging mode;
  means for receiving, from the subject, an echoed component of the transmitted ultrasound pulse signal to produce a reception signal; and
  means for producing a plurality of frames of tomographic images for the same portion of the subject using the reception signal.

17. The apparatus of claim 16, wherein the echoed component includes a component of the ultrasound pulse signal echoed by an ultrasound contrast medium of which substantial constituent is made up of micro-bubbles, the medium being injected into the subject.

18. The apparatus of claim 17, wherein the transmission frame rate changing means is configured to change the transmission frame rate according to a given time-sequential rule.

19. The apparatus of claim 16, wherein the transmission frame rate changing means has at least one of means for allowing an operator to specify time-sequential values of the transmission frame rate arbitrarily and means for selecting a desired time-sequential frame rate value from a plurality of time-sequential frame rate values preset as the transmission frame rate.

20. The apparatus of claim 17, further comprising means for selecting two frames of tomographic images from the plurality of frames of tomographic images produced; and
  means for calculating pixel by pixel differences in pixel amount between the two frames of tomographic images selected.

21. The apparatus of claim 16, wherein the changing means has means for issuing a command to change the transmission rate and placed external to the apparatus.

22. A method of diagnosing a subject using an ultrasound pulse signal transmitted into the subject under a transmitting condition, wherein an echo component of the transmitted ultrasound pulse signal is received to produce a reception signal, comprising the steps of:
  obtaining the reception signal as the transmitting condition is controlled to have different amounts of transmission power; and
  determining an optimum amount of the transmission power defined by the transmitting condition on the obtained reception signal.

23. A method of diagnosing a subject using an ultrasound pulse signal transmitted into the subject under a transmitting condition, an ultrasound contrast medium being injected into the subject, wherein an echo component of the transmitted ultrasound pulse signal is received to produce a reception signal, comprising the steps of:
  obtaining the reception signal as the transmitting condition is controlled to have different amounts of transmission power;
  determining an optimum amount of the transmission power defined by the transmitting condition on the obtained reception signal;
  controlling the transmitting condition so as to raise an amount of the transmission power from the optimum amount and then restore the raised amount to the optimum amount;
  obtaining the reception signal after the restoration of the transmission power to the optimum amount; and
  measuring data indicative of a time intensity curve (TIC) on the reception signal obtained after the restoration of the transmission power to the optimum amount.

24. A method of diagnosing a subject using an ultrasound pulse, comprising the steps of:
  transmitting the ultrasound pulse signal into a same portion of the subject at a transmission frame rate changed time-sequentially in a same imaging mode;
  receiving, from the subject, an echoed component of the transmitted ultrasound pulse signal to produce a reception signal; and
  producing a plurality of frames of tomographic images at the same portion of the subject using the reception signal.

* * * * *